US006577700B1

(12) United States Patent
Fan et al.

(10) Patent No.: US 6,577,700 B1
(45) Date of Patent: Jun. 10, 2003

(54) NEURAL NETWORK BASED MULTI-CRITERIA OPTIMIZATION IMAGE RECONSTRUCTION TECHNIQUE FOR IMAGING TWO- AND THREE-PHASE FLOW SYSTEMS USING ELECTRICAL CAPACITANCE TOMOGRAPHY

(76) Inventors: Liang-Shih Fan, 1286 Castleton Rd. N, Columbus, OH (US) 43220; W. Warsito, 572 Stineheome Dr. #5, Columbus, OH (US) 43202

(*) Notice: Subject to any disclaimer, the term of this patent is extended or adjusted under 35 U.S.C. 154(b) by 4 days.

(21) Appl. No.: 09/887,276

(22) Filed: Jun. 22, 2001

(51) Int. Cl.$^7$ .................... A61B 6/03; G01N 27/04; G01N 27/22
(52) U.S. Cl. .................... 378/4; 378/901; 324/686; 324/691
(58) Field of Search .................... 378/4, 8, 210, 378/901; 324/698, 686, 691

(56) References Cited

U.S. PATENT DOCUMENTS

| 5,984,023 A | * 11/1999 | Sharma et al. ................. 175/50 |
| 6,003,620 A | * 12/1999 | Sharma et al. ................. 175/50 |
| 6,220,371 B1 | * 4/2001 | Sharma et al. ................. 175/50 |

FOREIGN PATENT DOCUMENTS

| GB | 2302408 A | * 1/1997 | .......... G01N/27/22 |
| GB | 2329476 A | * 3/1999 | ............ G01F/1/74 |

OTHER PUBLICATIONS

Beck, M.S. 1995, "Selection of sensing techniques" in *Process Tomography—Principles Techniques and Applications*, Butterworth–Heinemann, Oxford, UK, 41–48.

Beck, M.S. and Williams, R.A. 1996, "Process tomography: a European innovation and its applications," *Meas. Sci. Technol.* 7, 215–224.

Dyakowski, T., Luke, S.P., Ostrowski, K.L. and Williams, R.A. 1999, "On–line monitoring of dense phase flow using real time dielectric imaging," *Powder Technol.* 104, 287–295.

Dyakowski, T., Edwards, R.B. Xie, C.G., and Williams, R.A. 1997, "Application of capacitance tomography to gas–solid flows," *Chem. Eng. Sci.* 52, 2099–2110.

Fan, L.–S. 1989, *Gas–liquid–solid fluidization engineering*, Butterworth, Stoneham, MA.

Fan, L.–S., Yang, G.Q, Lee, D.J. Tsuchiya, K. and Luo, X. 1999, "Some aspects of high–pressure phenomena of bubbles in liquids and liquid–solid suspensions," *Chem. Eng. Sci.* 54, 4681–4709.

(List continued on next page.)

*Primary Examiner*—David V. Bruce
(74) *Attorney, Agent, or Firm*—Standley & Gilcrest LLP

(57) ABSTRACT

A new image reconstruction technique for imaging two- and three-phase flows using electrical capacitance tomography (ECT) has been developed based on multi-criteria optimization using an analog neural network, hereafter referred to as Neural Network Multi-criteria Optimization Image Reconstruction (NN-MOIRT)). The reconstruction technique is a combination between multi-criteria optimization image reconstruction technique for linear tomography, and the so-called linear back projection (LBP) technique commonly used for capacitance tomography. The multi-criteria optimization image reconstruction problem is solved using Hopfield model dynamic neural-network computing. For three-component imaging, the single-step sigmoid function in the Hopfield networks is replaced by a double-step sigmoid function, allowing the neural computation to converge to three-distinct stable regions in the output space corresponding to the three components, enabling the differentiation among the single phases.

46 Claims, 8 Drawing Sheets

OTHER PUBLICATIONS

George, D.L., Torczynski, J.R., Shollenberger, K.A., O'hern, T.J. and Ceccio, S.L. 2000, *Quantitative tomographic measurements of opaque multiphase flows Sandia, Report SAND2000–0441*, Sandia Nat'l Laboratories.

Gordon, R., Bender, R. and Herman, G.T. 1970, "Algebraic reconstruction techniques (ART) for three–dimensional electron microscopy and X–ray photography," *J. Theor. Biol.* 29, 471–481.

Haow, J.S. and Nicoletti, P. 1992, "Observations of fluidized–bed coalescence using capacitance imaging," *Powder Technol.* 69, 255–277.

Herman, G.T. 1980, *Image reconstruction from projections*, Academic Press, NY, USA.

Hopfield, J. 1984, "Neurons with graded response have collective computation properties like those of two–state neurons," *Proc. Nat'l Academy of Sci.* 81, May, 3088–3092.

Hopfield, J. and Tank. D. 1985, " "Neural" computation of decisions in optimization problems," *Biological Cybernetics* 52, 141–152.

Isaksen, Ø. 1996, "A review of reconstruction techniques for capacitance tomography," *Meas. Sci. Technol.* 7, 325–337.

Johansen, G.A., Frøystein, T., Hjertaker, B.T. and Olsen, Ø. 1996, "A dual sensor flow imaging tomographic system," *Meas. Sci. Technol.* 7, 297–307.

Liang, Y. 1996, "Combinatorial optimization by Hopfield networks using adjusting neurons," *Information Sci.* 94, 261–276.

Liu, S., Fu, L. and Yang, W.Q. 1999, "Optimization of an iterative image reconstruction algorithm for electrical capacitance tomography," *Meas. Sci. Technol.* 10, L37–L39.

Mwambela, A.J., Isaksen, Ø. And Johansen, G.A. 1997, "The use of entropic thresholding methods in reconstruction of capacitance tomography data," *Chem. Eng. Sci.* 52, 2149–2159.

Nooralahiyan, A.Y. and Hoyle, B.S. 1997, "Three–compoent tomographic flow imaging using artificial neural network reconstruction," *Chem. Eng. Sci.* 52, 2139–2148.

Ostrowski, K.L., Luke, S.P. and Williams, R.A. 1997, "Simulation of the performance of electrical capacitance tomography for measurement of dense pneumatic conveying," *Chem. Eng. J.* 68, 197–205.

Paik, J.K and Katsagelos, A.K. 1992, "Image reconstruction using a modified Hopfield networks," *IEEE Trans. Image Process.* 1, 49–63.

Process Tomography Ltd. 1999, *Application Note AN4—An iterative method for improving ECT images*, PTL, Cheshire, UK.

Reinecke, N. and Mewes, D. 1996, "Recent development and industrial/research applications of capacitance tomography," *Meas. Sci. Technol.* 7, 1996, 233–246.

Smith, K., Krishnamoorthy, M. and Palaniswami, M. 1996, "Neural versus traditional approaches to the location of interacting hub facility," *Location Sci.* 4, 155–171.

Su, B., Zhang, Y., Peng. L., yao, D. and Zhang, B. 2000, "The use of simultaneous iterative reconstruction technique fr electrical capacitance tomography," *Chem. Eng. J.* 77, 37–41.

Sun, Y., Li. J.–G. and yu, S.–Y. 1995, "Improvement on performance of modified Hopfield neural network for image restoration," *IEEE Trans. Image Process.* 4, 688–692.

Wang, Y. 1997, "Multicriteria neural network approach to turbulent image reconstruction," *Optics Commun.* 143, 279–286.

Wang, Y. 1998, "Neural network approach to image reconstruction from projections," *Int. J. Imaging system and Technol.* 9, 381–387.

Warsito, Ohkawa, M., Kawata, N. and Uchida, S.: "Cross–sectional distributions of gas and solid holdups in slurry bubble column investigated by ultrasonic computed tomography", Chem. Eng. Sci. , vol. 54, 4711–4728 (1999).

Williams, R.A. and Beck, M.S. 1995, *Process Tomography—Principles, Techniques and Applications*, Butterworth–Heinemann, Oxford, UK.

Xie, C.G. 1995, "Image reconstruction," in *Process Tomography—Principles, Techniques and Applications*, Williams, R.A. and Beck, M.S., Butterworth–Heinemann, Oxford, UK, 281–323.

Xie, C.G., Huang, S.M., Hoyle, B.S., Thorn, R., Lean, C., Snowden, D. and Beck, M.S. 1992, "Electrical capacitance tomography for flow imaging system model for development of image reconstruction algorithms and design of primary sensor," *IEE Proc. G* 139, 89–98.

Yang, W.Q., Spink, D.M., York, T.A. and McCann, H. 1999, "An image reconstruction algorithm based on Landweber's iteration method for electrical–capacitance tomography," *Meas. Sci. Technol.* 10, 1065–1069.

Yang, W.Q., Stott, A.L., Beck, M.S. and Xie, C.G. 1996, "Development of capacitance tomography imaging systems for oil pipeline measurements", *Int. J. Multiphase Flow* 2, Supplem. 1, 144–145.

Zhou, Y.–T, Chellapa, R., Vaid. and Jenkins, B.K. 1998, "Image restoration using a neural network," *IEEE Trans. Acoust. Speech Signal Process.* 36, 1141–1151.

* cited by examiner

NEURAL NETWORK BASED MULTI-CRITERIA OPTIMIZATION IMAGE RECONSTRUCTION TECHNIQUE FOR IMAGING TWO- AND THREE-PHASE FLOW SYSTEMS USING ELECTRICAL CAPACITANCE TOMOGRAPHY

TECHNICAL FIELD OF INVENTION

This invention relates to electrical capacitance tomography. Specifically, the invention relates to a new image reconstruction technique for imaging two- and three-phase flows using electrical capacitance tomography (ECT).

BACKGROUND OF INVENTION

Applications of process tomography as a robust non-invasive tool for direct analysis of the internal characteristics of process plants in order to improve the design and operation of the equipment have increased in number in recent years (Williams and Beck, 1995, Beck and Williams, 1996). Process tomography involves utilization of tomographic imaging methods to manipulate data from remote sensors to obtain precise quantitative information from inaccessible locations. The need for tomography in industrial applications is analogous to the medical need for body scanners. A tomographic technique involves two basic tasks: (1) the acquisition of measurement signals from sensors located on the periphery of an object, such as a process vessel or column; and (2) the process of abstracting the measurement signals, which reveals information on the nature and distribution of components within the sensing zone, to form a cross-sectional image of the object. The task of generating image from the measurement signals is also known as tomographic reconstruction. The basic components of a tomographic instrument are, therefore, embodied in a sensor system, a signal/data acquisition system and a computer system for measurement control, image reconstruction and display.

Successful implementation of a tomographic technique lies on the selection of a sensor system deployed for the specified application and the tomographic image reconstruction algorithm suited to the sensor selected. A variety of sensing methods can be employed based on measurements of transmission, diffraction or electrical phenomena using radiation, acoustic or electrical sensors (Beck, 1995). For the purpose of multiphase flow imaging in process industries, one of the most critical things may be the speed of the technique to capture the real time data of the turbulent fluctuation in the flow field. In this regard, electrical capacitance tomography (ECT) is considered to be the most powerful tool among other available tomographic techniques because of its high-speed capability, low construction cost, high safety and suitability for small or large vessels. Currently commercially available electrical capacitance tomography systems could capture up to 100 image frames per second, compared to corresponding electrical resistance tomography (ERT) of 2 image frames per second, or X-ray computer tomography (CT) of only one image every 2 seconds.

ECT is gaining acceptance as a laboratory and industrial tool to analyze multiphase systems. Early efforts with ECT have been concerned with the imaging of two-phase stratified flows in industrial pipelines, especially oil-gas and oil-water flows from offshore oil wells (Yang et al., 1996), manufacturing processes involving gas-solid systems such as pneumatic conveyers (Ostrowski et al., 1997, Dyakowski et al., 1999) and gas-solid fluidizations (Dyakowski et al., 1997, Halow and Nicoletti, 1992, Wang et al., 1995), and trickle bed reactors for measuring water content (Reinecke and Mewes, 1997, 1998). However, application of the technique to more complex multiphase flow systems such as bubbly flows in gas-liquid as well as gas-liquid-solid systems which are widely used in chemical processes (Fan, 1989) is very limited. ECT has prospective uses for applications to gas-liquid and gas-liquid-solid systems in real chemical processes, since they are mostly using organic liquids (Fan et al., 1999), which are non-conductive, rather than water which is a widely used model liquid in laboratories. The implementation of the technique would considerably further research in these fields since the information provided by the rapid online imaging method offers a means to address long-standing problems in the modeling, optimization and control of these processes.

However, the most critical problems that still challenge the application of the technique to such systems may be the relatively low spatial resolution and the accuracy of the reconstructed image using existing techniques. Most work currently done by researchers is focused on efforts to address these problems. While leaving the problem on the spatial resolution to other researchers working on sensor hardware, this work deals with a reconstruction technique aimed at improving the accuracy of the reconstructed image. The selection of image reconstruction technique suited to the sensor is highly important, because it determines the quality of the image that gives the information required to analyze the flow system. In the case of capacitance tomography, unfortunately, the reconstruction problem is non-linear, so that commonly used and commercially available and well-developed reconstruction techniques for linear tomographies based on electromagnetic radiation as widely used in the medical field are not directly applicable to the non-linear problem. Although many studies have been reported on the development of image reconstruction techniques for capacitance tomography, the reconstructed results using the techniques reported so far are still more qualitative rather than quantitative. For application to relatively complex multiphase system such as bubbly flows, high accuracy of the reconstruction results is especially necessary. There is an urgent need for development of an accurate reconstruction technique for capacitance tomography to meet the requirement of real chemical process applications.

Multi-modal Tomographic Techniques for Three-phase Flow Imaging

Tomographic technique for two-phase flow imaging is referred to as single modal tomography, where the requisite sensed signal contains only one parameter in the object space, (e.g., energy absorption (electromagnetic radiations), permittivity (capacitance sensor) or conductivity (impedance sensor) (Nooralahiyan and Hoyle, 1997)). In a three-phase system, the requisite sensed signal contains two or more parameters that require a multi-sensing method. The tomographic technique for imaging a three-phase flow system is referred to as multi-modal tomography. Most of the tomographic techniques developed so far are for single-modal systems, which are not readily applicable to three-phase systems. There are three strategies to perform three-phase imaging using a tomographic technique: (1) by combination of two different single-modal sensing systems, (2) using an inherently multi-modal sensing system, and (3) by means of a single-modal sensing system having a reconstruction technique capable of differentiating between three phases in the object space (Warsito et al., 1999).

An example of the first approach is the use of electrical capacitance tomography combined with Gamma-ray tomography for imaging a multi-component composition of gas, oil and water in a pipeline (Johansen et al., 1996). Water has a permittivity approximately 40 times to that of oil, or 80 times to that of gas, so that it can be easily differentiated from gas and oil using the electrical capacitance tomography. The gas distribution is then determined using Gamma-tomography which is responsive to the large density difference between the gas and the liquids. George et al. (2000) used electrical resistance tomography (ERT) combined with Gamma densitometry tomography (GDT) to measure the gas and solid concentration (holdup) profiles in three-phase bubble column. They employed dry air as the gas phase, water with sodium nitrate as the liquid phase, and both polystyrene and glass-beads for the solid phase. Polystyrene is an electrical insulator like air but has a gamma attenuation coefficient similar to water, so that ERT is influenced by both the solid and gas phases while GDT is primarily sensitive to the gas alone. In the reconstruction, the gas volume fraction profile from GDT is subtracted from the insulating phase profile determined by ERT to get first-approximations of volume fractions of the three components. Glass has a gamma attenuation coefficient significantly different from both air and water, so that the first-order approximation does not hold in this case. Instead, the gamma attenuation formulas and the Maxwell-Hewitt conductivity relation for mixed materials must be solved as a set of simultaneous equations to reconstruct the volume fraction profiles of the three phases. However, the primary problem of using this approach arises because the measurements using the combined techniques are not conducted simultaneously in the same object domain, so that the reconstructed profiles may be severely distorted. In addition, this approach is complex to implement and impractical with respect to the overall cost.

The second approach uses a single sensing technique, which is an inherently multi-modal system capable of differentiating between two or more species in the object space. This approach is advantageous because all the information required is available using the same measuring technique and image reconstruction. An example of this approach is the dual-frequency ultrasonic method implemented by Warsito et al. (1995) to measure gas and solid concentration distributions in a three-phase bubble column. The gas and solid concentrations are obtained by measuring time-of-flights of ultrasonic pulse beams in high and low frequencies. In high frequency (10 MHz~), the response of the gas bubble on the time-of-flight is negligible, allowing the measurement of the solid phase alone. The gas phase is then calculated by subtracting the time-of-flight in lower frequency (1~3 MHz) by the time-of-flight due to the solid phase. Another technique using ultrasonic tomography with two-parameter sensing is implemented by Warsito et al. (1997, 1999) to measure the cross-sectional distributions of gas and solid concentrations in a gas-liquid-solid bubble column. They evaluated both the attenuation and the time-of-flight of a single ultrasonic pulse beam transmitted through the three-phase medium to construct a set of simultaneous equations involving gas and solid concentrations. The gas and the solid concentrations are obtained by solving the two equations. The major advantage of using this technique is that the gas and the solid concentrations are measured simultaneously. However, the technique is limited to relatively low concentrations of gas or solid, lower than 20% for both. The use of optical tomography coupled with spectral analysis and electrical tomography by exploring the potential of impedance spectroscopy and dielectric spectroscopy also shows potential for multi-modal tomography systems (Beck, 1995).

The third approach uses a single modal sensing system but with a reconstruction technique capable of differentiating between three species in the object domain. An example is the use of electrical capacitance tomography with a neural-network-based image reconstruction technique as proposed by Nooralahiyan and Hoyle (1997). They used a single layer feed forward neural network with double-step sigmoid function to replace a single-step sigmoid function in the neural-network computing to enable the identification of gas bubbles and water drops in oil environment. Though the network training is extremely time consuming, once well trained the neural network is very fast when used for prediction (reconstruction). However, the problem is that the feed forward neural network needs prior knowledge of the flow pattern for training before any measurements can be taken. This makes the technique impractical for real applications when training is not possible, particularly for the real time imaging of complex flows where the pattern is highly fluctuated and unknown before an exact image is obtained.

Principles of Electrical Capacitance Tomography (ECT)

An ECT system can be divided into three basic components: (1) capacitance sensor, (2) sensing electronics for data acquisition and (3) computer system for image reconstruction, interpretation and display. The capacitance sensor consists of a number of electrodes located on the periphery of the process vessel (FIG. 1). If the number of electrodes is ne, there will be ne(ne−1)/2 combinations of independent capacitance measurements between electrode-pairs. The measured capacitance is a function of the dielectric constant (permittivity) filling the space between the electrodes in the pair. Fundamental problems in ECT are associated with the process of image reconstruction from the measured capacitances based on Poisson's equation given by (Xie et al., 1992, Xie, 1995)

$$\in(x,y)\nabla^2\Phi(x,y)+\nabla\in(x,y)\nabla\Phi(x,y)=0 \qquad (1)$$

where $\in(x,y)$ and $\Phi(x,y)$ are the dielectric constant and the electrical potential distributions, respectively. This second-order, elliptic-type partial differential equation has either Dirichlet-type or Neumann-type typical boundary conditions. The dielectric field is given by $$E=-\nabla\Phi(x,y) \qquad (2)$$

By applying the Gauss law, the charge at the detector electrode induced by the source electrode in the ith electrode-pair (see FIG. 1) can be calculated by the following expression:

$$Q_i=\int\in(x,y)E\cdot\hat{n}dl \qquad (3)$$

where $\Gamma_i$ is a closed curve enclosing the detector electrode and $\hat{n}$ is the unit normal vector to $\Gamma_i$. The capacitance between the electrode-pair, $C_i$, can be calculated by $$C_i = \frac{Q_i}{\Delta V_i} = \frac{1}{\Delta V_i}\oint_{\Gamma_i} \varepsilon(x,y)E\cdot\hat{n}dl \qquad (4)$$

where $*V_i$ is the voltage difference between the source and the detector electrodes of electrode-pair i.

Equation (4) relates the dielectric constant (permittivity) distribution, $\in(x,y)$, to the measured capacitances $C_i$. That is, for a given medium distribution $\in(x,y)$ and the boundary conditions, the capacitances can be calculated (e.g., using a finite element method). This task is referred to as a forward problem. The image reconstruction process is an inverse problem involving the estimation of the permittivity distribution from the measured capacitances. However, as seen from this equation, it is difficult to obtain an explicit expression that relates the measured capacitances to the fraction and position of the dielectric components inside the pipe. Some reconstruction techniques developed for ECT are overviewed in the following section.

Image Reconstruction Techniques for ECT

Since there is no general solution method for the forward problem (in which the equation becomes non-linear), approximation methods are usually used. The most common one is using the so-called sensitivity model (Huang et al., 1989, Xie et al., 1992). The model is based on the electrical network superposition theorem in which the domain (the cross section of the sensor) is subdivided into a number of pixels, and the response of the sensor may be found as a sum (linear model) of interactions which will result when the permittivity of only one pixel in the domain is changed by a known amount. This is similar to the first order series expansion approach for 'hard field' tomography (Herman, 1980). However, this model only holds if the difference between the dielectric constants of the constituent materials being imaged is small (high-to-low permittivity ratio is less than 6). According to this model, eq. (4) can be written as a matrix expression as:

$$C=SG \quad (5)$$

where C is the measured capacitance matrix, G is the image vector (permittivity distribution) and S is the so-called sensitivity map. Equation (5) is regarded as the linear forward projection (LFP). The sensitivity map is calculated as $$S_{ij} = \left(\frac{A_{max}}{\Delta\varepsilon_0 A_j}\right)\frac{C_i^{(H,j)} - C_i^L}{C_i^H - C_i^L} \quad (6)$$

i=1, 2, ..., M
j=1, 2, ..., M where $C_i^{(H,j)}$ is the capacitance value of the ith electrode-pair when pixel j inside the sensor is a material with high permittivity and the rest is material of low permittivity. M is the number of electrode-pair combinations, and N is the number of pixels in the object space. $\Delta\varepsilon_0$ is the permittivity difference between the high and low permittivity materials. $A'_j$ is the area of element j and $A_{max}$ is the largest element of all $A_j$. The sensitivity map is constructed by numerically solving equation (4) using a finite-element method (FEM) or by an experimental method using a dielectric rod placed at different positions inside the cross section of the sensor and measuring the capacitance between the electrode pair. The sensitivity map is necessary to solve the inverse problem using linear back projection (LBP) algorithm (Huang et al., 1989, Xie et al., 1992). Here, the image vector G is obtained from the following matrix transformation:

$$G=S^T C \quad (7)$$

where $S^T$ is the matrix transpose of S.

The reconstructed image using LBP is blurred, demonstrating a smoothing effect on the sharp transitions between the different dielectric constants. This effect is typical in reconstruction results using the linear back-projection technique, because the gray level of each pixel in the image is formed from a set of overlapping projections. To reduce the blurring effect, a filter function as commonly used in filtered-back projection algorithm for linear tomography or a thresholding procedure is usually applied (Xie et al., 1992, Mwambela et al., 1997), however, only slight improvements have been achieved by these procedures.

A great demand for high quality images generated by ECT has led many researchers to develop reconstruction techniques based on iterative algorithms (Reinecke and Mewes, 1996, 1997, Isaken, 1996, Yang, 1997, Liu et al., 1997, Su et al., 2000). Iterative algorithms may be classified into two groups: an algebraic reconstruction technique (ART) type and an optimization type. The ART type is a modification of the original technique developed for linear tomography by combining the linear reconstruction technique with the sensitivity model. The image reconstruction problem with using ART is estimating the image vector (permittivity distribution) G such that the estimated capacitances C*(G) $\leq$C, given a measurement vector C. The following form generally represents ART type algorithms:

$$G^{(k+1)} = G^{(k)} + \alpha^{(k)} S^T (C - C^*(G^{(k)})) \quad (8)$$

where $G^{(k)}$ is the estimated permittivity vector in the k-th iteration, $\alpha$ is a relaxation factor, also called a gain factor or weighting factor. The initial estimate of the permittivity vector $G^{(0)}$ is calculated using LBP by eq. (7). For the sake of convenience, eq. (8) is normalized as $$\tilde{G}^{(k+1)} = \tilde{G}^{(k)} + \alpha^{(k)} \tilde{S}^T (\tilde{C} - \tilde{C}^*(\tilde{G}^{(k)})) \quad (9)$$

where $$\tilde{G}_j = \frac{G_j - \varepsilon_{0L}}{\varepsilon_{0H} - \varepsilon_{0L}}, \quad \tilde{S}_{ij} = \frac{S_{ij}}{\sum_j S_{ij}}, \quad (10)$$

$$\tilde{S}_{ij}^T = \tilde{S}_{ji} = \frac{S_{ji}}{\sum_i S_{ij}}, \quad \tilde{C}_i = \frac{C_i - C_i^L}{C_i^H - C_i^L}$$

i=1,2, ..., M
j=1,2, ..., N

For simplicity, in the rest of this paper the normalization notation (~) is omitted, and all the above parameters, otherwise stated, use the normalized forms.

Many ART type algorithms for ECT used by researchers differ slightly from each other in the structures of the relaxation factor $\alpha$ and the procedure used to correct the estimated permittivity values. Commercially available reconstruction software developed by PTL (UK, 1999) uses a constant relaxation factor and LFP technique (eq. 5) to solve the forward problem in the correction term for the estimated permittivity, i.e.:

$$C^*(G^{(k)}) = SG^{(k)}. \quad (11)$$

This is simply LBP used in an iterative manner, similar to iterative back projection techniques for linear tomography. Reinecke and Mewes (1996, 1997) use a correction factor $$\left(\sum_j S_{ij}^2\right)^{-1}$$

instead of the relaxation factor, similar to ART for linear tomography (Gordon et al., 1970), and use a finite difference technique to solve the forward problem in the correction term to replace the LFP method. It should be noted that, unlike Gordon ART for 'hard field' (linear) tomography, in electrical capacitance tomography problems the electrical field spreads all over the measured cross-section allowing no distinct border between the pixels which contribute to the ith pair capacitance measurement and those which do not, due to the 'soft field' effect. Thus, for ECT, all of the capacitance data is typically used to update the pixel values. In this regard, the technique can also be referred to as simultaneous iterative reconstruction technique (SIRT) as used by Su et al. (2000). The technique used by Reinecke and Mewes (1997) has improved the accuracy of the reconstructed result, though the finite difference technique significantly increases the computation time. To improve the convergence performance, Su et al. (2000) determined a priori the relaxation factor in the form of:

$$\alpha^{(k)} = \alpha_0 + \frac{\beta}{k}, \quad (12)$$

where $\alpha_0$ and $\beta$ are positive constants. They also used LFP to solve the forward problem in the correction term in eq. (10). The choice of the relaxation factor has significantly improved the convergence performance, though there is still a smoothing effect in the region between different permittivities. Liu et al. (1999) used an optimal relaxation factor calculated by minimizing the error function $e^{(k+1)}=\|C-SG^{(k+1)}\|^2$ so that $$\frac{\partial e^{(k+1)}}{\partial \alpha^{(k)}} = 0.$$

Yang et al. (1999) determined the gain factor based on suitable convergence criterion:

$$\alpha^{(k)} = 2/\lambda_{max}, \quad (13)$$

where $\lambda_{max}$ is the maximum eigenvalue of $S^TS$. They replaced LFP with FEM to solve the forward problem in the correction term to improve both the image quality and the convergence rate, though this significantly increases the computation load.

The second group of iterative techniques is based on an optimization algorithm in which one or more objective functions are minimized or maximized. The objective functions, typically the least squared error sum and/or the maximum entropy function, are measures of the 'likelihood' with respect to the definition of the problem. Isaken and Nordtvetd (1996) proposed an optimization technique for ECT called model-based reconstruction (MOR). The MOR technique minimizes the least squared error sum between the measured capacitance and the estimation value calculated using model-based parameter chosen to represent the image pattern. Thus, a prior knowledge of the image pattern (permittivity distribution) is required for the pattern representation before the reconstruction is done. Mwambela et al. (1997) used the maximum entropy function to generate threshold values to address the 'smoothing' effect on LBP results.

With regard to minimizing an objective function like MOR, ART is a kind of optimization technique aimed at finding a least squared error between the measured and the estimated capacitances. Such criteria, however, does not necessarily determine the image vector G because image reconstruction is an ill-posed problem as there are fewer independent measurements than unknown pixel values. Therefore, there may be more than one possible alternative image. Another reason why such a solution is not necessarily very good is that the least squared criterion does not contain any information regarding the nature of a 'desirable' solution (Herman, 1980). Therefore, more than one objective function is required to be minimized simultaneously to choose the 'best compromise-solution' from possible alternatives.

In this work, a multi-criteria optimization based image reconstruction technique for imaging gas-liquid two-phase flows using electrical capacitance tomography is developed. The reconstruction technique is a combination of multi-criteria optimization image reconstruction technique (Wang et al., 1996, Wang, 1997, 1998) for linear tomography and the LBP technique. The multi-criteria optimization image reconstruction problem is then solved using modified Hopfield model dynamic neural-network computing. It is believed that this is the first application of multi-criteria optimization technique to a 'soft field' tomography problem.

The reconstruction technique for the two-phase system is extended to three-phase system by introducing a double-step sigmoid in the modified Hopfield network. By using the double-step sigmoid function, the calculation is permitted to converge to three-different stable regions in the output space corresponding to the three-different phases, enabling differentiation among the three components. This technique has a major advantage over the feed-forward neural network based image reconstruction technique as used by Noorala-hiyan and Hoyle (1997) because there is no network training needed. Thus, it can be applied to any multiphase system without prior knowledge on the flow pattern.

SUMMARY OF THE INVENTION

The image reconstruction technique of the present invention is based upon multi-criteria optimization using an analog neural network (NN-MOIRT). This reconstruction technique is a combination of multi-criteria optimization image reconstruction techniques for linear tomography, and the so-called linear back projection (LBP) technique commonly used for capacitance tomography. The multi-criteria optimization image reconstruction problem is solved using Hopfield model dynamics neural-network computing.

A plurality of sensors is placed around the periphery of a conduit through which flows a two- or three-phase fluid system. The sensors collect image measurements of the fluid between sensors. That is to say, the plurality of sensors will provide n(n−1)/2 image measurements, where n is the number of sensors. The image measurements shall collectively be referred to as 'data' or 'image measurement data'.

The present invention presents a novel method for image reconstruction comprising obtaining data, processing the data by application of a linear back projection algorithm with a Hopfield neural network, and displaying the processed data on a display device.

Suitable forms of data include, but are not limited to, capacitance data, conductance data, x-ray data, gamma-ray data, ultrasonic data and optical data. It is preferred that the data is capacitance data or conductance data. It is most preferred that the data is capacitance data.

The linear back projection algorithm may be an iterative back projection algorithm (ILBP). The linear back projection algorithm preferably comprises at least one function to minimize. It is most preferred that the linear back projection algorithm comprises three functions to minimize: a negative entropy function, a weighted square error function and a sum of non-uniformity and peakedness functions.

It is preferred that the Hopfield model neural network is modified to include a penalty function that permits a temporary increase in the descending evolution of the Hopfield network energy to allow escape from local minima.

Suitable display devices include, but are not limited to: monitors, projectors, printers and plotters. Other display devices may be suitable for displaying the data and will be known to those skilled in the art.

The present invention provides a method for obtaining a cross-sectional image of a two-phase fluid flowing through a conduit. A sensor is comprised of a transmitter and a receiver. The method comprises acquiring image measurement data from at least two sensors peripherally located on the interior of the conduit, the at least two sensors defining a cross-section of the conduit. The image measurement data is next sent to a processing unit. The image measurement data processing comprises the simultaneous minimization of a negative entropy function of an image given by $$f_1(G) = \gamma_1 \sum_{j=1}^{N} G_j \ln G_j$$

where $\gamma_1$ is a normalized constant between 0 and 1; a weighted square error function given by $$f_2(G) = \frac{1}{2}\gamma_2 \sum_{i=1}^{M} \left( \sum_{j=1}^{N} S_{ij} G_j - C_i \right)^2$$

where $\gamma_2$ is a normalized constant between 0 and 1; and a sum of non-uniformity and peakedness functions given by $$f_3(G) = \frac{1}{2}\gamma_3 (G^T X G + G^T G)$$

where $\gamma_3$ is a normalized constant between 0 and 1. The simultaneous minimization is accomplished by application of a Hopfield model neural network given by $$E(G) = \sum_{l=1}^{3} \omega_l f_l(G) + \sum_{i=1}^{M} \Psi(z_i) + \sum_{j=1}^{N} \frac{1}{R_j} \int_{0}^{G_j} f_\Sigma^{-1}(G) dG$$

wherein normalized permittivity values are mapped into output variables using a single sigmoid function given by $$f_\Sigma(u_j) = \frac{1}{1 + \exp(-\beta u_j)},$$

to force convergence to a binary output. The Hopfield model neural network further comprising a penalty function $\Psi(z_i)$ defined as $$\Psi(z_i) = \begin{cases} 0 & \text{if } z_i \le 0 \\ \alpha z_i & \text{if } z_i > 0 \end{cases}$$

where $$z_i = \sum_{j=1}^{N} S_{ij} G_j - C_i$$

with $\alpha(t) = \alpha_0 + \xi \exp(-\eta t)$ where $\alpha_0$, $\xi$, and $\eta$ are positive constants. The penalty function prevents convergence at local minima. The output variables are then sent to a display device to display a cross-sectional image of the two-phase fluid flowing through the conduit.

The two-phase fluid flowing through the interior of the conduit may consist of any combination of solids and gases; solids and liquids; liquids and gases; two different solids; two different liquids; or two different gases.

The present invention also provides for a method for obtaining a cross-sectional image of a three-phase fluid flowing through a conduit having an interior. The method comprises acquiring image measurement data from at least two sensors peripherally located on the interior of the conduit, the at least two sensors defining a cross-section of said conduit. The image measurement data is then sent to a processing unit. The image measurement data processing comprises the simultaneous minimization of a negative entropy function of an image given by $$f_1(G) = \gamma_1 \sum_{j=1}^{N} G_j \ln G_j$$

where $\gamma_1$ is a normalized constant between 0 and 1; a weighted square error function given by $$f_2(G) = \frac{1}{2}\gamma_2 \sum_{i=1}^{M} \left( \sum_{j=1}^{N} S_{ij} G_j - C_i \right)^2$$

where $\gamma_2$ is a normalized constant between 0 and 1; and a sum of non-uniformity and peakedness functions given by $$f_3(G) = \frac{1}{2}\gamma_3 (G^T X G + G^T G)$$

where $\gamma_3$ is a normalized constant between 0 and 1. The simultaneous minimization is accomplished by application of a Hopfield model neural network given by $$E(G) = \sum_{l=1}^{3} \omega_l f_l(G) + \sum_{i=1}^{M} \Psi(z_i) + \sum_{j=1}^{N} \frac{1}{R_j} \int_{0}^{G_j} f_\Sigma^{-1}(G) dG$$

wherein normalized permittivity values are mapped into output variables using a double sigmoid function given by $$f_\Sigma(u_j) = f_{\Sigma 1}(u_j) + f_{\Sigma 2}(u_j),$$

where $$f_{\Sigma 1}(u_j) = \frac{\rho_1}{1 + \exp(-\beta_1 (u_j + \xi_1))},$$

$$f_{\Sigma 2}(u_j) = \frac{\rho_2}{1 + \exp(-\beta_2 (u_j + \xi_2))},$$

$\rho_1$ and $\rho_2$ are positive constants, $\beta_1$ and $\beta_2$ are steepness gains of sigmoid functions $f_{\Sigma 1}$ and $f_{\Sigma 2}$, and $\xi_1$ and $\xi_2$ are parameters, where the double sigmoid function purpose is to force convergence to a tertiary output. The Hopfield model further comprises a penalty function $\Psi(z_i)$ defined as $$\Psi(z_i) = \begin{cases} 0 & \text{if } z_i \le 0 \\ \alpha z_i & \text{if } z_i > 0 \end{cases}$$

where $$z_i = \sum_{j=1}^{N} S_{ij} G_j - C_i$$

with $\alpha(t)=\alpha_0+\xi \exp(-\eta t)$ where $\alpha_0$, $\xi$, and $\eta$ are positive constants. The penalty function prevents convergence at local minima. The output variables are then sent to a display device to display a cross-sectional image of the three-phase fluid flowing through the conduit.

The three-phase fluid flow consists of any combination of solids, liquids and/or gases.

The present invention further provides a method for obtaining a cross-sectional image of a multiphase fluid flowing through a conduit having an interior using a Hopfield type neural network by acquiring image measurement data for fluid flowing through the conduit. The image measurement data is acquired by at least two sensors peripherally located on the interior of the conduit, the at least two sensors defining a cross-section of the conduit. The Hopfield model neural network is initialized by (1) choosing an initial state of neurons; (2) setting at least one steepness gain factor; (3) initializing a penalty parameter; and (4) initializing an initial gain factor. The image vector is updated accordingly. The iterative process stops when $|G_j(t+\Delta t)-G_j(t)|^2 \leq e$ for all neurons, where $|G_j(t+\Delta t)-G_j(t)|^2$ is error and e is a termination scalar set by an operator. The image vector is then displayed on a suitable display device.

It is preferred that the initial state of neurons is set to zero. For a two-phase fluid flow, it is preferred that the steepness gain factor is set to two. For a three-phase fluid flow, it is preferred that both steepness gain factors are set to 2. It is further preferred that the initial state of the gain factor and the initial state of the penalty factor are each experimentally determined.

For a two-phase fluid flow, it is preferred that the image vector is updated by calculating coefficients of objective functions:

$$\gamma_1^{(t+\Delta t)} = \left[\sum_{j=1}^{N} G_j(t) \ln G_j(t)\right]^{-1},$$

$$\gamma_2^{(t+\Delta t)} = \left[\frac{1}{2}\|SG(t) - C\|^2\right]^{-1},$$

$$\gamma_3^{(t+\Delta t)} = \left[\frac{1}{2}G^T(t)sG(t) + \frac{1}{2}G^T(t)G(t)\right]^{-1};$$

updating weights $\omega_1, \omega_2, \omega_3$ for every iteration as follows:

$$\omega_i^{(t+\Delta t)} = \frac{\Delta \omega_1^{(t)} / \Delta \omega_i^{(t)}}{\sum_{i=1}^{3} \Delta \omega_1^{(t)} / \Delta \omega_i^{(t)}},$$

$\Delta \omega_1^{(t)} = f_i(G(t+\Delta t)) - f_i(G(t))$, (i=1,2,3) where $f_1$ is a negative entropy function, $f_2$ is a weighted square error function and $f_3$ is a sum of non-uniformity and peakedness functions of an image; and calculating an image vector $G_j(t+\Delta t)$, where $G_j(t+\Delta t) = G_j(t) + f'_\Sigma(u)u'_j(t)\Delta t$, $f'_\Sigma(u) = df_\Sigma(u_j)/du_j$ and $u'_j(t) = du_j(t)/dt$.

For a three-phase fluid flow, it is preferred that the image vector is updated by calculating coefficients of objective functions:

$$\gamma_1^{(t+\Delta t)} = \left[\sum_{j=1}^{N} G_j(t) \ln G_j(t)\right]^{-1},$$

$$\gamma_2^{(t+\Delta t)} = \left[\frac{1}{2}\|SG(t) - C\|^2\right]^{-1},$$

$$\gamma_3^{(t+\Delta t)} = \left[\frac{1}{2}G^T(t)sG(t) + \frac{1}{2}G^T(t)G(t)\right]^{-1};$$

updating weights $\omega_1, \omega_2, \omega_3$ for every iteration as follows:

$$\omega_i^{(t+\Delta t)} = \frac{\Delta \omega_1^{(t)} / \Delta \omega_i^{(t)}}{\sum_{i=1}^{3} \Delta \omega_1^{(t)} / \Delta \omega_i^{(t)}},$$

$\Delta \omega_i^{(t)} = f_i(G(t+\Delta t)) - f_i(G(t))$, (i=1,2,3) where $f_1$ is a negative entropy function, $f_2$ is a weighted square error function and $f_3$ is a sum of non-uniformity and peakedness functions of an image; and calculating an image vector $G_j(t+\Delta t)$, where $G_j(t+\Delta t) = f_\Sigma(u_j(t+\Delta t)) = G_j(t) + [f_{\Sigma 1}(u_j)(1 - f_{\Sigma 1}(u_j)) + f_{\Sigma 2}(u_j)(1 - f_{\Sigma 2}(u_j))]u'_j(t)\Delta t$, $$f_{\Sigma 1}(u_j) = \frac{\rho_1}{1 + \exp(-\beta_1(u_j + \xi_1))},$$

$$f_{\Sigma 2}(u_j) = \frac{\rho_2}{1 + \exp(-\beta_2(u_j + \xi_2))},$$

$\rho_1 = \tilde{\in}_{OM}$, and $\rho_2 = 1 - \tilde{\in}_{OM}$, where $\tilde{\in}_{OM}$ is the normalized relative permittivity of the medium-permittivity material.

DETAILED DESCRIPTION OF THE PREFERRED EMBODIMENT(S)

Multi-criteria Optimization Problem

Figure 1:
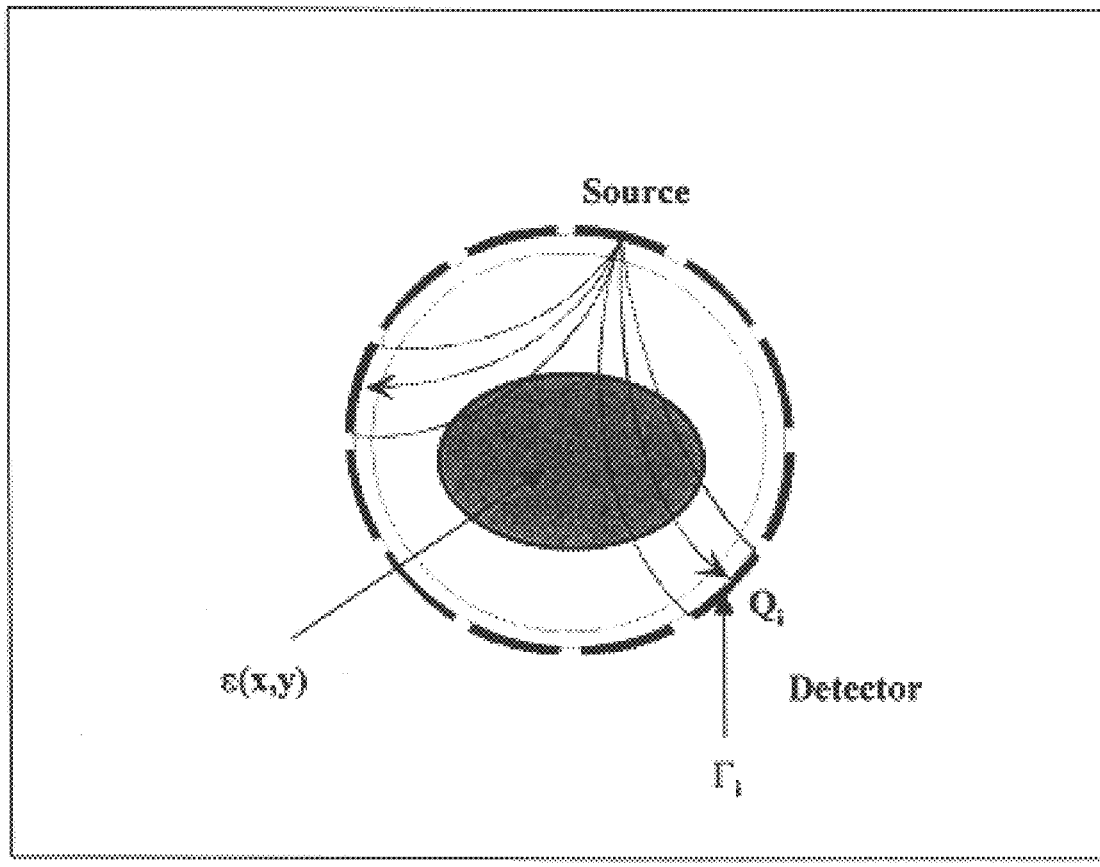
FIG. 1 illustrates the principle of a capacitance measuring system for electrical capacitance tomography (ECT).

Now, considering the truncation errors due to linearization in LBP technique and inaccuracy in the physical measurement, eq. (5) can be rewritten as $$C = SG + e \quad (14)$$

where e is an M-dimensional error vector. Then, the reconstruction problem is to again find methods for estimating the image vector (permittivity distribution) G from the capacitance measurement vector C, and minimizes the error e. Since we obviously do not know e, the problem is to find a "compromise solution" of the system under certain conditions (criteria), such that $$SG \leq C \quad (15)$$

The criteria that have been used for image reconstruction problem are usually of the form: Choose as the "solution" of eq. (15) an image vector G for which the value of some function $f_i(G)$ is minimal, and if there is more than one G which minimizes $f_i(G)$ choose among these one for which the value of some other function $f_i(G)$ is minimal (Herman, 1980). The multi-criteria optimization based solution method is usually to find an image which (a) has the largest entropy; (b) has the least weighted square error between the measured data set and the estimated value calculated from the reconstructed image; (c) is local and smooth and has a relatively small peakedness (Wang, 1998). Therefore, the choices for the optimization functions (objective functions) should fulfill these "desirable" criteria for the reconstruction image.

The first objective function is the negative entropy function of the image (Wang, 1998):

$$f_1(G) = \gamma_1 \sum_{j=1}^{N} G_j \ln G_j, \quad (16)$$

where $\gamma_1$ is a normalized constant, $0 < \gamma_1 < 1$. The objective function $f_1(G)$ is a measure of the global smoothness of the reconstructed image. The use of the maximum entropy criterion is usually justified by arguments that of all the pictures that satisfy the primary criterion, the maximum entropy solution should have the smallest information content. Minimizing $f_1(G)$ would result in maximizing the positive entropy function $(-f_1(G))$. Hence, the objective function $f_1(G)$ must be minimized (the entropy is maximized) so as to preserve a smoothed reconstruction image.

The second objective function $f_2(G)$ is the weighted square error function between the measured capacitance data set C and the estimated capacitance from the reconstructed image, i.e.:

$$f_2(G) = \frac{1}{2}\gamma_2 \|SG - C\|^2 = \frac{1}{2}\gamma_2 \sum_{i=1}^{M} \left( \sum_{j=1}^{N} S_{ij} G_j - C_i \right)^2 \quad (17)$$

where $\gamma_2$ is a normalized constant, $0 \leq \gamma_2 \leq 1$. This objective function must be minimized to ensure that the capacitance values calculated from the reconstructed pixel values are as close as possible to the measurement data.

The third objective function, $f_3(G)$, is the sum of the non-uniformity and peakedness functions of an image (Herman, 1980), i.e.:

$$f_3(G) = \frac{1}{2}\gamma_3 (G^T X G + G^T G) \quad (18)$$

where $\gamma_3$ is a normalized constant, $0 < \gamma_3 < 1$. X is an N×N non-uniformity matrix, also called as smoothing matrix, whose (j,k) component $X_{j,k}$ for the basic smoothing matrix is defined by $$X_{j,k} = \begin{cases} x_1 & \text{if } k = j \\ x_2 & \text{if } k \in E_j \\ x_3 & \text{if } k \in V_j \\ 0 & \text{otherwise} \end{cases} \quad (1 \leq j \leq N) \quad (19)$$

here $E_j$ denote the set of indices of the pixels which have exactly one edge in common with the jth pixel, and $V_j$ denote the set of indices of pixels which have exactly one vertex in common with the jth pixel in the N×N image digitization. $(x_1, x_2, x_3)$ are called the smoothing weights, whose values are $(1, -\frac{1}{8}, -\frac{1}{8})$ for basic smoothing matrix. The objective function $f_3(G)$ should be minimized to ensure the preservation of local smoothness and small peakedness in the reconstructed image.

Again, the multi-criteria optimization for the reconstruction problem is to choose an image vector G for which the value of multi-objective function $F(G) = [f_1(G), f_2(G), f_3(G)]^T$ is minimized simultaneously. This can be realized by the weighted sum technique stated mathematically as:

$$\begin{cases} \underset{G \in \Pi}{\text{minimize}} \Phi(G) \equiv \sum_i w_i f_i(G), \quad (i = 1, 2, 3) \\ \text{so that } SG - C \leq 0. \end{cases} \quad (20)$$

where $w_i$ is a weight operating on the objective function $f_i(G)$ and can be interpreted as "the relative weight or worth" of the objective compared to the other objectives, i.e.

$$\sum_{i=1}^{3} w_i = 1. \quad (21)$$

Π is the feasible set of constrained decisions defined by linear constraints as:

$$\Pi = G \in R^N | SG \leq C, G \geq 0, C \in R^M \quad (22)$$

Solution Using Hopfield Dynamic Neural Networks

In the present invention we use an analog neural network based on Hopfield model to solve the optimization problem (eq. (20)). Hopfield model neural networks, or simply Hopfield nets (Hopfield, 1984), have been used to successfully address many difficult optimization problems (Hopfield and Tank 1985), including image restoration (Paik and Katsaggelos, 1992, Sun et al., 1995, Zhou et al., 1995) and image reconstruction (Wang, 1997, 1998). Their advantages over more traditional optimization technique lie in their potential for rapid computational power when implemented in electrical hardware, and the inherent parallelism of the network (Smith et al., 1996).

To solve the optimization problem using the neural network technique, we shall map the normalized permittivity values $G_j$ into the output variable $v_j$ for neuron j bounded by 0 and 1. The output variable is a continuous and monotonic increasing function of the internal state of the neuron:

$$G_j = v_j = f_\Sigma(u_j), \tag{23}$$

where $u_j$ is the internal state variable of the neuron j. Function $f_\Sigma$ is called the activation function, typically of the form:

$$f_\Sigma(u_j) = \frac{1}{1+\exp(-\beta u_j)}, \tag{24}$$

where $\beta$ is a steepness gain factor that determines the vertical slope and the horizontal spread of the sigmoid-shape function. By using such a non-linear sigmoid-shape activation function, the neuron output is forced to converge to a binary output 1 or 0. However, when the output values in between are equally expected as the extreme values as in application of tomography for concentration measurement, the following linear activation function is better to use.

$$f_\Sigma(u_j) = \begin{cases} 0 & \text{if } u_j \le -\xi/\beta \\ \beta u_j + \xi & \text{if } -\xi/\beta < u_j < 1-\xi/\beta \\ 1 & \text{if } 1-\xi/\beta \le u_j \end{cases} \tag{25}$$

where $\beta$ and $\xi$ become the slope and the intercept of the line, respectively.

In Hopfield model dynamics neural networks the neuronal activities of the output $v_j$ as well as the input $u_j$ depend on time t. The evolution of the networks is determined by the N-coupled ordinary differential equations (Hopfield, 1984):

$$C_{0j} \frac{du_j}{dt} = -\frac{\partial E(v)}{\partial v_j} \tag{26}$$

where $C_{0j}$ is an associated capacitance in the jth neuron in the Hopfield nets with time constant $\tau(\tau = R_{0j}C_{0j}, R_{0j}$ is the associated resistance), and E is the system energy of the Hopfield networks. The time derivative of E(v) is $$\frac{dE(v)}{dt} = \sum_{j=1}^{N} \frac{\partial E(v)}{\partial v_j} \frac{dv_j}{dt} = -\sum_{j=1}^{N} C_{0j} \frac{du_j}{dt} \frac{dv_j}{dt} = \tag{27}$$

$$-\sum_{j=1}^{N} C_{0j} f'_\Sigma(u_j) \left(\frac{du_j}{dt}\right)^2 = -\sum_{j=1}^{N} C_{0j} (f_\Sigma^{-1}(v_j))' \left(\frac{dv_j}{dt}\right)^2$$

Since $C_{0j}$ is positive and the sigmoid function $f_\Sigma(u_j)$ and its inverse function $f_\Sigma^{-1}(v_j)$ are monotonic increasing (the gradients are positive), this sum is nonnegative and then $$\frac{dE}{dt} \le 0; \quad \frac{du_j}{dt} = \frac{dv_j}{dt} = 0$$

for all j when $t \to \infty$. Clearly, the time evolution of the network system is headed towards the stable state of minimizing the energy of the system (i.e. Hopfield network has a monotonic descending nature). Hopfield and Tank (1985) have shown that this character can be used to solve optimization problems in which some objective functions are minimized. Typically, the neural network energy function is made equivalent to the objective function of the optimization problem which is to be minimized, while constraints of the problem are included in the energy function as penalty terms (Smith et al., 1996, Liang, 1996). Then, the corresponding neural networks energy function to the optimization problem in eq. (20) can be written as $$E(G) = \sum_{l=1}^{3} \omega_l f_l(G) + \sum_{i=1}^{M} \Psi(z_i) + \sum_{j=1}^{N} \frac{1}{R_j} \int_0^{G_j} f_\Sigma^{-1}(G) dG \tag{28}$$

where N is the number of neurons in the Hopfield nets, and is equal to the number of pixels in the digitized image, and M is the number of capacitance data measurements. The first term in eq. (28) is the interactive energy among neurons. The second term is related to the constraint violation, which must be minimized. The third term in eq. (28) encourages the network to operate in the interior of the N-dimensional unit cube $\{0 \le G_j \le 1\}$ that forms the state space of the system. In the second term, the constrained neuron i have the nonlinear input-output relation described by the function $\Psi(z_i)$ defined as $$\frac{d\Psi}{dz_i} = \delta(z_i) = \begin{cases} 0 & \text{if } z_i \le 0 \\ \alpha z_i & \text{if } z_i > 0 \end{cases} \tag{29}$$

where $$z_i = \sum_{j=1}^{N} S_{ij} G_j - C_i \tag{30}$$

here, $\alpha$ is a large penalty parameter. The function $\Psi(z_i)$ provides for the output of the neuron j to be a large positive value when the corresponding constraint equation is being violated. Since the Hopfield network is a monotonic descent technique as described above, it will converge to the first local minimum it encounters. Unfortunately, a minimum of the energy function does not necessarily correspond to a constrained minimum of the objective function due to the fact that there are likely to be several terms in the energy function that contribute to many local minima. By introducing the penalty function, it will permit temporary increases in the descending evolution of the Hopfield network energy in order to allow escape from local minima. The form of penalty parameter a is chosen as:

$$\alpha(t) = \alpha_0 + \xi \exp(-\eta t) \tag{31}$$

Here $\alpha_0$, $\xi$ and $\eta$ are positive constants. This modified Hopfield network provides a mechanism for escaping local minima by varying the direction of motion of the neurons in such a way that a large ascent step is taken by the penalty function in initial iterations and is less likely as the algorithm proceeds.

Now substituting the multi-objective functions (eqs. (16), (17) and (18)) into eq. (31) one obtains the overall energy function as $$E(G) = \omega_1 \gamma_1 \sum_{j=1}^{N} G_j \ln G_j + \frac{1}{2} \omega_2 \gamma_1 \|SG - C\|^2 + \tag{32}$$

$$\frac{1}{2} \omega_3 \gamma_3 (G^T X G + G^T G) + \sum_{i=1}^{M} \Psi(z_i) + \sum_{j=1}^{N} \frac{1}{R_j} \int_0^{G_j} f_\Sigma^{-1}(G) dG$$

For simplicity, choosing $R_{0j}=R_0$ and $C_{0j}=C_0$, and redefining $$R_0 C_0, \frac{\gamma_1}{C_0},$$

$$\frac{\gamma_2}{C_0},$$

and $$\frac{\gamma_3}{C_0}$$

as, $\tau$, $\gamma_1$, $\gamma_2$ and $\gamma_3$, respectively, the time evolution of the internal state variable of neurons in the networks become:

$$u'(t) = -\frac{1}{C_0}\nabla E(G) = -\frac{u(t)}{\tau} - [\omega_1\gamma(1+\ln G(t)) + \frac{\omega_2\gamma_2}{\sigma^2}S^T z(t) + \omega_3\gamma_3(XG(t)+G(t))+S^T\delta(z(t))] \quad (33)$$

where, $$\nabla E(G) = \left[\frac{\partial E(G)}{\partial G_1}, \frac{\partial E(G)}{\partial G_2}, \ldots, \frac{\partial E(G)}{\partial G_N}\right]^T,$$

$u(t)=[u_1(t),u_2(t),\ldots,u_N(t)]^T,$
$G(t)=[G_1(t),G_2(t),\ldots,G_N(t)]^T,$
$z(t)=[z_1(t),z_2(t),\ldots,z_M(t)]^T.$ The image vector (permittivity values) $G_j$ becomes the output of jth neuron and is calculated from the sigmoid function (eqs.(24) or (25)):

$$G_j(t)=f_\Sigma(u_j(t)), j=1,2,\ldots,N \quad (34)$$

However, unlike in multi-layer feed forward (MLF) neural networks the parameter $u_j$, here, is calculated by solving systems of eq.(33) using, for example Euler's method. Here, we set $C=1.0$, until the system converges to a stationary state. And we take $\tau=1.0$ so that time is measured in units $\tau$, and time step length $\Delta t=0.01$. The iteration process of the internal state variable of the jth neuron and the corresponding pixel value of the image are, respectively, given by:

$$u_j(t+\Delta t)=u_j(t)+u'_j(t)\Delta t \quad (35)$$

$$G_j(t+\Delta t)=f_\Sigma(u_j(t+\Delta t))=G_j(t)+f'_\Sigma(u)u'_j(t)\Delta t \quad (36)$$

where $f'_\Sigma(u)=df_\Sigma(u_j)/du_j$ and $u'_j(t)=du_j(t)/dt$. Using eq.(24) for the sigmoid function, eq. (41) can be rewritten as:

$$G_j(t+\Delta t)=G_j(t)+\beta G_j(t)[1-G_j(t)]u'_j(t)\Delta t. \quad (37)$$

Or using eq. (25) for the sigmoid function, eq.(36) simply becomes $$G_j(t+\Delta t)=G_j(t)+\beta u'_j(t)\Delta t. \quad (38)$$

The stopping rule usually used is when the changes in the firing rates become insignificant, i.e. for all pixels $|G_j(t+\Delta t)-G_j(t)|<e$, where $e<<1$.

Three-phase Reconstruction

As seen from eqs. (37) and (38), the convergence performance is determined by the steepness gain factor $\beta$. Reducing $\beta$ will result in reducing the correction term in eqs. (37) or (38) and consequently will slow the convergence. In contrast, a large value of $\beta$ results in a larger contribution to the correction term, forcing the network to take large steps in the output space of the neuron, and again, convergence is not guaranteed. The optimum value of $\beta$ is usually obtained experimentally. Since the value of $\beta$ also determines the interpolation ability in the center of the range, there will be only two stable regions in the output space (normalized permittivities of 0 and 1). Thus, for three-phase component imaging, a single-step sigmoid function with only two stable regions in the output space is inadequate to reconstruct three-phase components that require convergence in three stable regions corresponding to the three permittivity values. Alternatively, the following double-step sigmoid function similar to that used by Nooralahiyan and Hoyle (1997) is implemented.

$$f_\Sigma(u_j)=(u_j)+f_{\Sigma 2}(u_j), \quad (39)$$

where $$f_{\Sigma 1}(u_j)=\frac{\rho_1}{1+\exp(-\beta_1(u_j+\xi_1))}, \quad (40)$$

$$f_{\Sigma 2}(u_j)=\frac{\rho_2}{1+\exp(-\beta_2(u_j+\xi_2))}, \quad (41)$$

and $\rho_1$ and $\rho_2$ are positive constants that control the vertical range and shift to obtain a unipolar function. $\beta_1$ and $\beta_2$ are steepness gains of sigmoid functions $f_{\Sigma 1}$, and $f_{\Sigma 2}$ and determine, respectively, the lower and upper slopes in the vertical steps of the unipolar function. $\xi_1$ and $\xi_2$ are parameters that determine the input range to adjust the horizontal shift to obtain the unipolar function. The parameters $\rho_1$ and $\rho_2$ are chosen such that the lower, central and upper stable regions are corresponding to the normalized lowest, medium and highest permittivities of the three materials, i.e. 0, $\tilde{\epsilon}_{0M}$, and 1, respectively. Here, $\tilde{\epsilon}_{0M}$ is the normalized relative permittivity of the medium permittivity material, and defined as $$\tilde{\epsilon}_{0M} = \frac{\epsilon_{0M}-\epsilon_{0L}}{\epsilon_{0H}-\epsilon_{0L}}, \quad (42)$$

where $\epsilon_{0L}$, $\epsilon_{0M}$ and $\epsilon_{0H}$ are, respectively, the relative permittivies of the lowest, medium and highest permittivity materials. Then, the parameter $\rho_1$ and $\rho_2$ are, respectively, calculated as $$\rho_1=\tilde{\epsilon}_{0M} \quad (43)$$

$$\rho_2=1-\tilde{\epsilon}_{0M} \quad (44)$$

Figure 2:
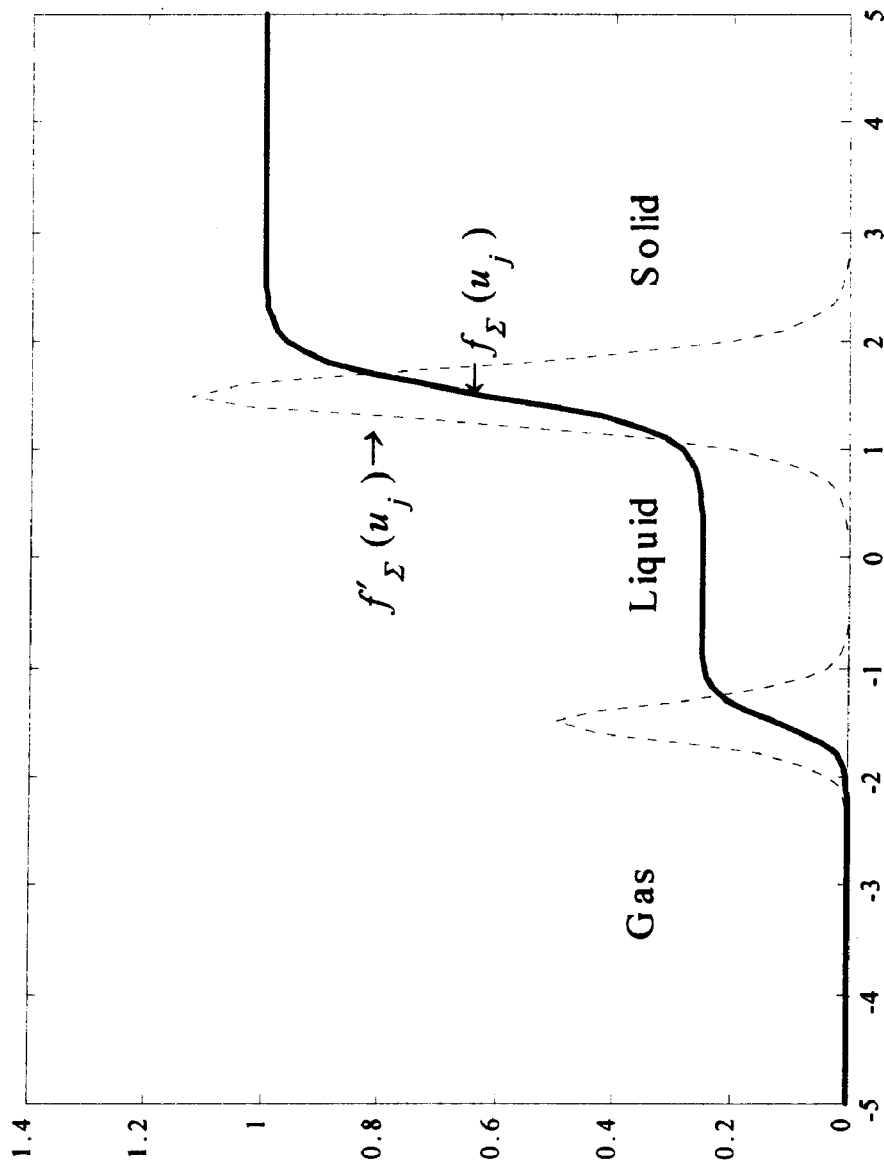
FIG. 2 illustrates the double-step sigmoid function for the differentiation of three phases: gas, liquid and solid.

The double-step sigmoid function with its derivative along the output range is shown in FIG. 2. Then, the iteration process of the image pixel value for the three-phase reconstruction becomes:

$$G_j(t+\Delta t)=f_\Sigma(u_j(t+\Delta t))=G_j(t)+[f_{\Sigma 1}(u_j)(1-f_{\Sigma 1}(u_j))+f_{\Sigma 2}(u_j)(1-f_{\Sigma 2}(u_j))]u'_j(t)\Delta t \quad (45)$$

By using the double-sigmoid function it enables better convergence for the three output values across a continuous range giving three distinct and stable regions required for three-phase reconstruction. Unlike the feed forward neural network implemented by Nooralahiyan and Hoyle (1997), the reconstruction based on the analog neural network proposed here utilizes the property of time evolution of the network towards state equilibrium of the state for all neurons from a given arbitrary initial condition. Thus, prior knowledge of the image structure to be reconstructed is not required, however, the computation time is much longer than the feed forward neural network due to the iterative process and the high computation load of the multi-criteria objective functions.

Simulations

We have tested the neural network based multi-criteria optimization technique for capacitance tomography proposed in this work on model permittivity distributions to investigate the performance of the technique for two- as well as three-phase systems imaging. A twelve electrode capacitance sensor system as shown in FIG. (1) is used to simulate the capacitance measurement based on a finite element method (FEM). A 66 measured capacitances data set is obtained from the 12 electrode-pair combination. The image is reconstructed on 32×32 digitized image pixels. The neural network approach to image reconstruction technique based on multi-criteria optimization for image reconstruction using ECT is summarized as follows:

1. Initialization step. Choose an initial state of neurons ($u_j(0)=0$; $v_j(0)=f_\Sigma(u_j(0))$). Set steepness gain factor $\beta=2$ (for three-phase reconstruction, we set $\beta_1=\beta_2=2$). The initial penalty parameter a and the initial gain factor $\zeta$ are the only parameters that significantly influence the convergence performance, and are obtained experimentally. In this work, we used $\alpha_0=7.0$ and $\zeta=5.0$ for all reconstruction, unless otherwise stated. To ensure the robustness of the technique to a noise, a Gaussian noise is added to the simulated capacitances data as follows:

$$\hat{C}_i = [1+N(\mu,\rho^2)]C_i$$

where $N(\mu,\rho^2)$ is a Gaussian distribution function with mean $\mu$ and variance $\rho^2$. Here we set $\mu=0$ and $\rho=0.05$. The initial weights are chosen to be $$\omega_1^{(0)} = \omega_2^{(0)} = \omega_3^{(0)} = \frac{1}{3}.$$

2. Updating step. The coefficients of the objective functions for every iteration step are calculated as follows:

$$\gamma_1^{(t+\Delta t)} = \left[\sum_{j=1}^{N} G_j(t)\ln G_j(t)\right]^{-1}, \quad \gamma_2^{(t+\Delta t)} = \left[\frac{1}{2}\|SG(t)-C\|^2\right]^{-1},$$

$$\gamma_3^{(t+\Delta t)} = \left[\frac{1}{2}G^T(t)sG(t) + \frac{1}{2}G^T(t)G(t)\right]^{-1}.$$

And the weights $\omega_1, \omega_2, \omega_3$ for every iteration step are updated as follows:

$$\omega_i^{(t+\Delta t)} = \frac{\Delta\omega_1^{(t)}/\Delta\omega_i^{(t)}}{\sum_{i=1}^{3} \Delta\omega_1^{(t)}/\Delta\omega_i^{(t)}},$$

$\Delta\omega_i^{(t)} = f_i(G(t+\Delta t)) - f_i(G(t))$, (i=1,2,3)

where $f_1 \sim f_3$ are objective functions in eqs. (16), (17) and (18), respectively. Then update the image vector using the iteration process in eqs. (36) or (38) for two-phase reconstruction and eq. (49) for three-phase reconstruction, respectively. Repeat this updating procedure until the error is minimized.

3. Stopping. The termination scalar is determined to be $e=10^{-4}$, and when the error $|G_j(t+\Delta t)-G_j(t)|^2 \leq e$ for all neurons (pixels) then stop.

Convergence Performance

Figure 3:
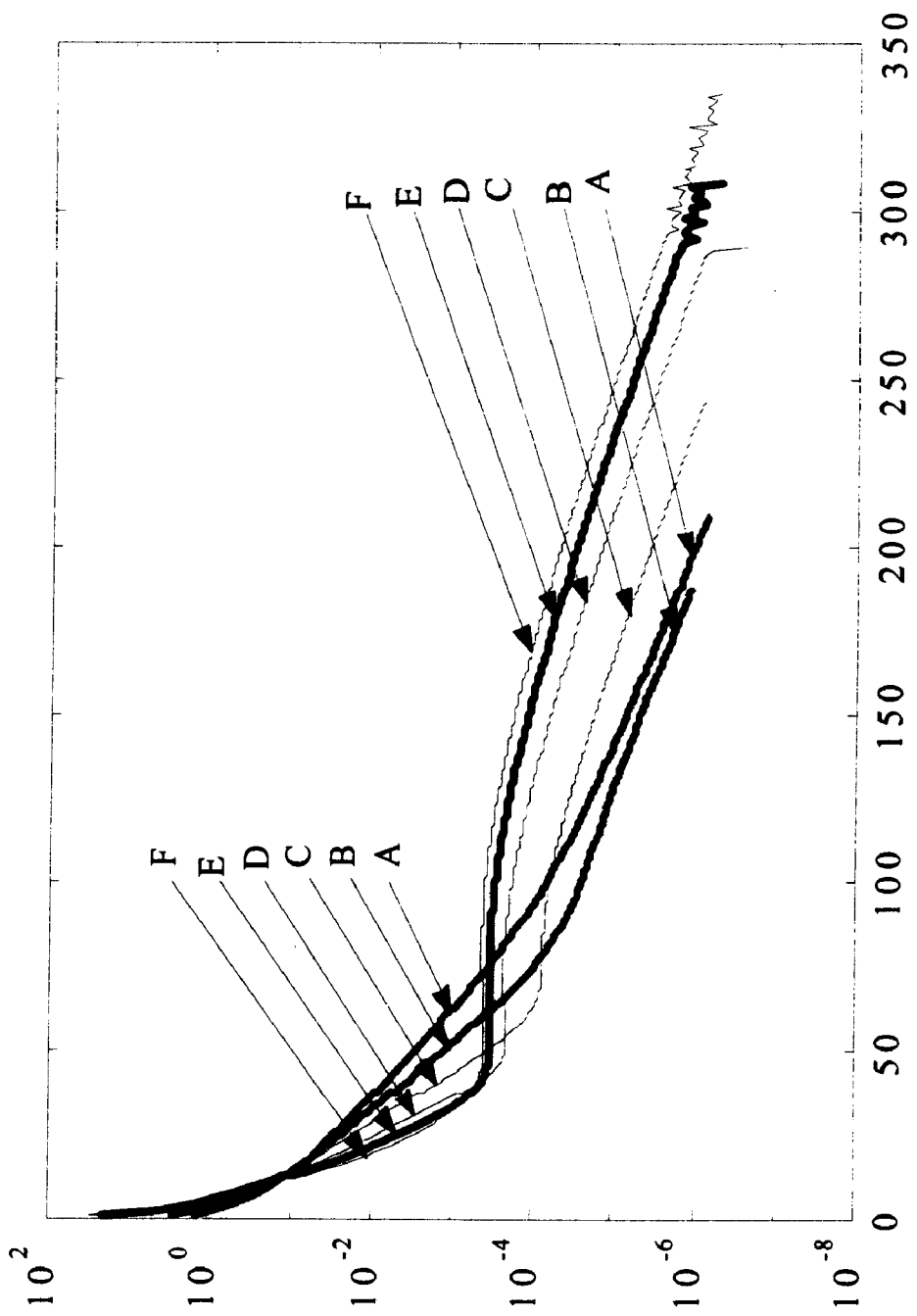
FIG. 3 illustrates the convergence performance of NN-MOIRT for various initial penalty factors $\alpha_0$ and initial gain factors $\zeta$: (A) $\alpha_0=5.0$, $\zeta=0$, (B) $\alpha_0=5.0$, $\zeta=2$, (C) $\alpha_0=5.0$, $\zeta=5$, (D) $\alpha_0=5.0$, $\zeta=10$, (E) $\alpha_0=5.0$, $\zeta=15$.

FIG. 3 shows the convergence performance of the NN-MOIRT when tested to a parabolic model distribution in FIG. 5(a) for various values of penalty factor $\alpha$. The ordinate is the squared error defined as $$\frac{1}{2}\sum_{j=1}^{N} |G_j(k+1) - G_j(k)|^2,$$

where k is the iteration. As seen from FIG. (3), when a constant penalty factor ($\alpha=\alpha_0$) is chosen, the convergence speed is monotone (i.e., the error decreases monotonically), resulting in a shorter pathway into the termination. However, as described above, due to the descending nature of evolution of the Hopfield network, the network energy may be stuck at the first local minima it encounters. From FIG. (3) it is seen that choosing a time dependent penalty factor as in eq.(31) will increase the convergence speed in the initial stage, but decrease it in the latter stages. It also allows a 'hill-climb' in the computation depending on the initial gain factor 4;, however, too large of an initial gain factor will cause the network to a step that is too large due to the large penalty parameter, resulting in oscillations near the convergence (i.e., a large penalty factor is not preferable near the convergence). Clearly, there are optimum values for the initial penalty factor $\alpha_0$ and the initial gain factor $\zeta$ which do not only allow a hill-climb to avoid a local minima, but also give a smooth convergence in the termination stage.

Figure 4A:
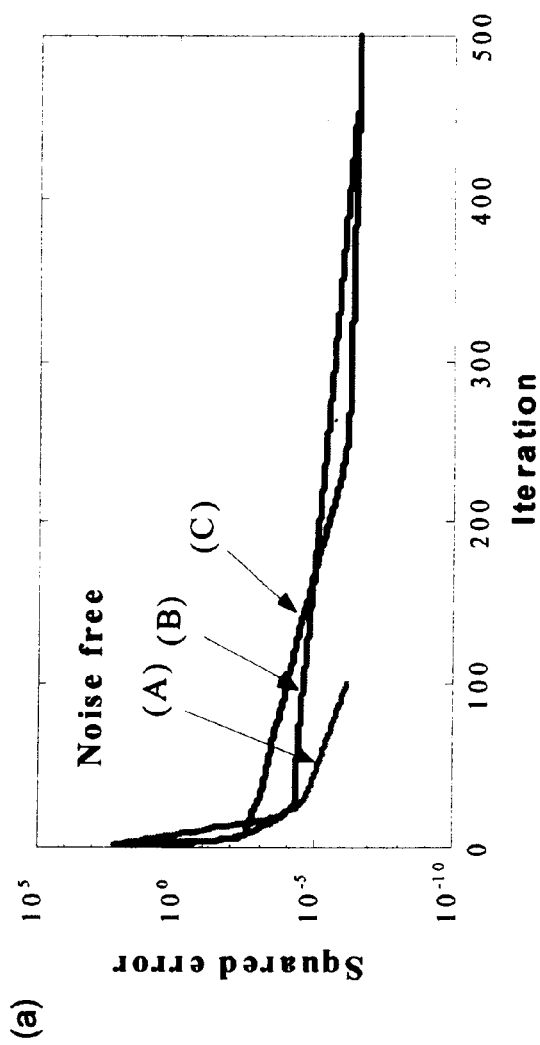
FIG. 4A is a comparison of convergence performances for three techniques in the absence of noise: (A) NN-MOIRT, (B) SIRT, (C) ILBP.
Figure 4B:
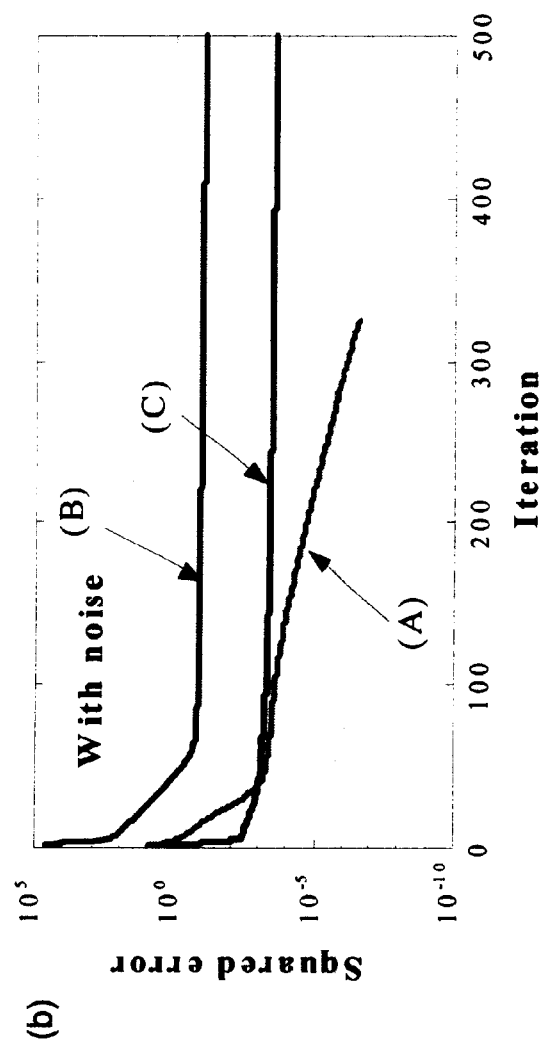
FIG. 4B is a comparison of convergence performances for three techniques in the presence of noise: (A) NN-MOIRT, (B) SIRT, (C) ILBP.

Comparisons of the convergence performance with other iterative techniques (Iterative Linear Back-Projection (ILBP) and Simultaneous Image Reconstruction Technique (SIRT)) are given in FIG. 4. ILBP is based on commercial software package developed by Process Tomography Limited (PFL, UK). SIRT for ECT is based on the work of Su et al. (2000). The termination parameters for the three techniques are set the same, i.e. $|G_j(k+1)-G_j(k)|<10^{-4}$ for all pixels. Referring to FIG. 4A, when no noise is added, there is no significant difference in the convergence performance between NN-MOIRT and the other two techniques in the initial stage, however, ILBP and SIRT require 3 to 4 times the iterations than NN-MOIRT to achieve convergence at the same termination level of the error. It should be noted that more iterations does not necessarily mean more computation time is needed. While the computation times per iteration for ILBP and SIRT are comparable (about one hundred iterations per second on PC with Pentium III processor), a little more time (about tens iterations per second on the same processor using matrix computation function imbedded in MATLAB programming) is needed for NN-MOIRT due to much more computation load. When a noise (Gausian) is added, ILBP as well as SIRT show extremely slow convergence, and seemingly will not achieve the convergence at the termination level given. As for NN-MOIRT there is no significant influence in the convergence performance despite of the existence of the noise.

Consistency of the Reconstructed Results

Figure 5:
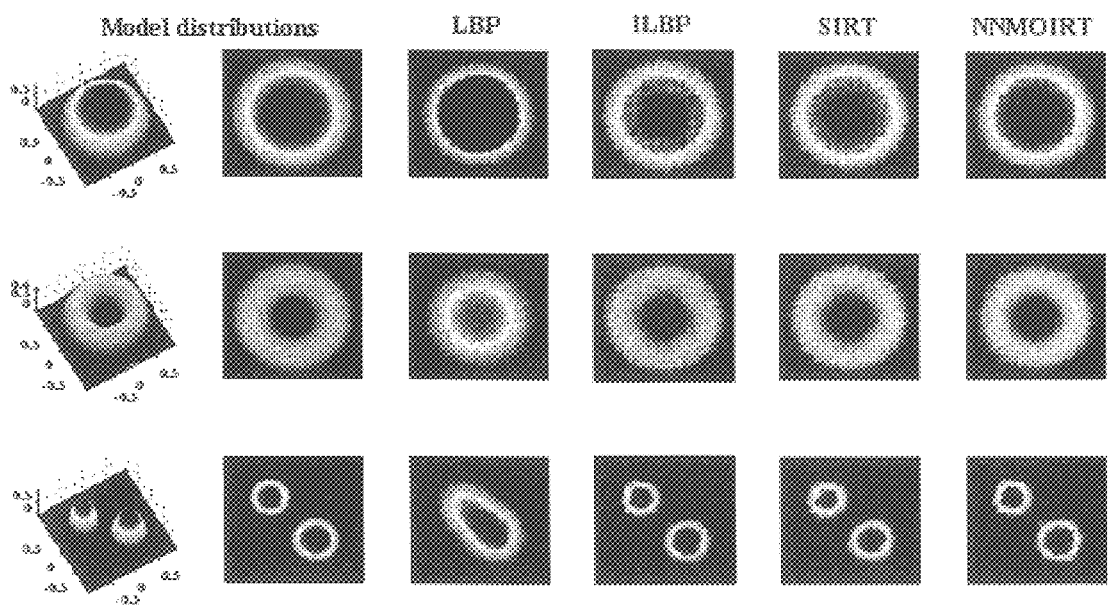
FIG. 5 is a comparison of reconstructed results using LBP, ILBP, SIRT and NN-MOIRT (noise free data).
Figure 6:
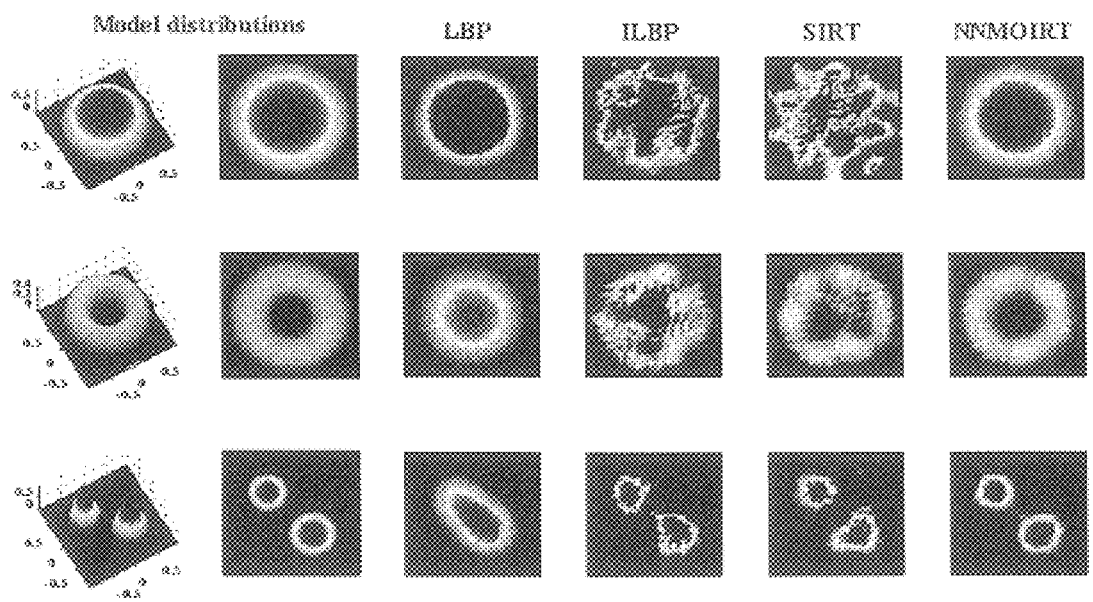
FIG. 6 is a comparison of reconstructed results using LBP, ILBP, SIRT and NN-MOIRT (noisy data).

FIGS. 5 and 6 show the reconstruction results for two-phase system using NN-MOIRT in comparisons with the other techniques. FIG. 5 shows the reconstruction results when no noise is added, while FIG. 6 is with noise. The first and second columns in FIGS. 5 and 6 show the model images (permittivity distributions in two-phase system). The subsequent columns show, respectively, the reconstructed images using LBP, ILBP, SIRT and NN-MOIRT. From FIG. 5, when there is no noise added, all the reconstruction techniques except LBP give relatively accurate reconstruction and high consistency to the original images (distributions). It is, however, NN-MOIRT that gives the best accuracy (with respect to the gray level (color)) and consistency (with respect to the shape), while LBP only gives a rough estimation of the original images (distributions).

Figure 7A:
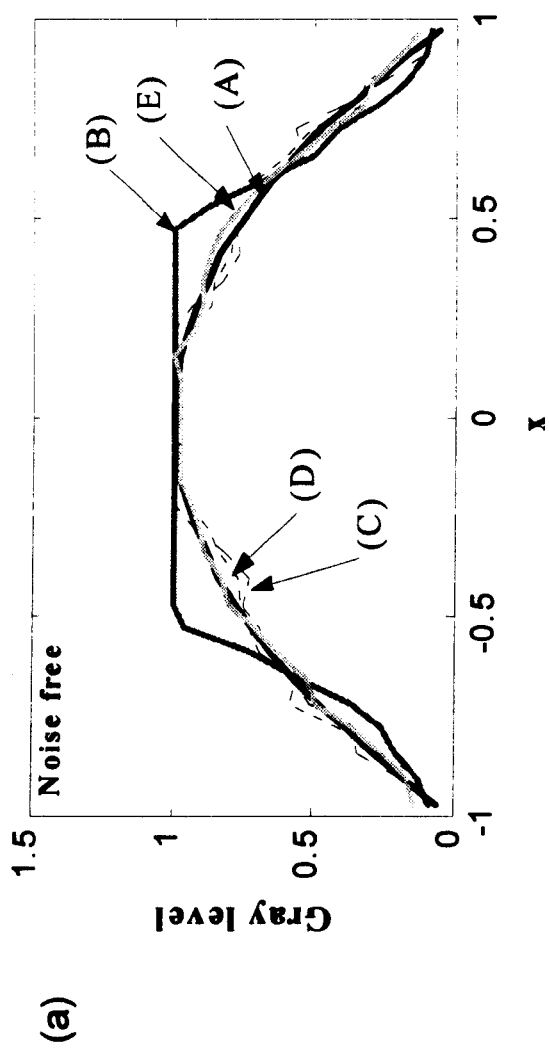
FIG. 7A is a quantitative comparison of reconstructed results using LBP, ILBP, SIRT and NN-MOIRT in the absence of noise: (A) Model distributions, (B) LBP, (C) ILBP, (D) SIRT and (D) NN-MOIRT.
Figure 7B:
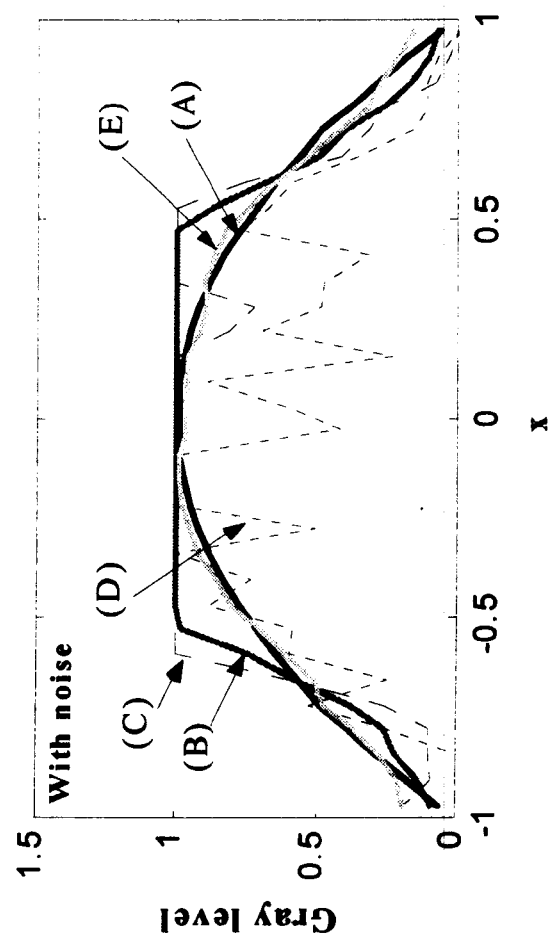
FIG. 7B is a quantitative comparison of reconstructed results using LBP, ILBP, SIRT and NN-MOIRT in the presence of noise: (A) Model distributions, (B) LBP, (C) ILBP, (D) SIRT and (D) NN-MOIRT.

When a noise is added (FIG. (6)), ILBP and SIRT no longer reconstruct the original images accurately, and again LBP only reconstructs the original images very roughly, though this technique is robust with respect to the noise. The reconstructed results by ILBP and SIRT are severely distorted from the original images. While using NN-MOIRT, the technique shows its robustness to noise. The technique still gives high accuracy and consistency despite the existence of the noise. Quantitative comparisons of the reconstructed results using the four techniques are also given in FIGS. 7(a) and (b) for noise free and when noise is added, respectively. The robustness of a reconstruction technique with respect to noise is crucial. A reconstruction technique that is too sensitive to noise causes the technique to become unrealistic because measurement data always contains noise varying in its magnitude.

Three-component Reconstruction

Figure 8:
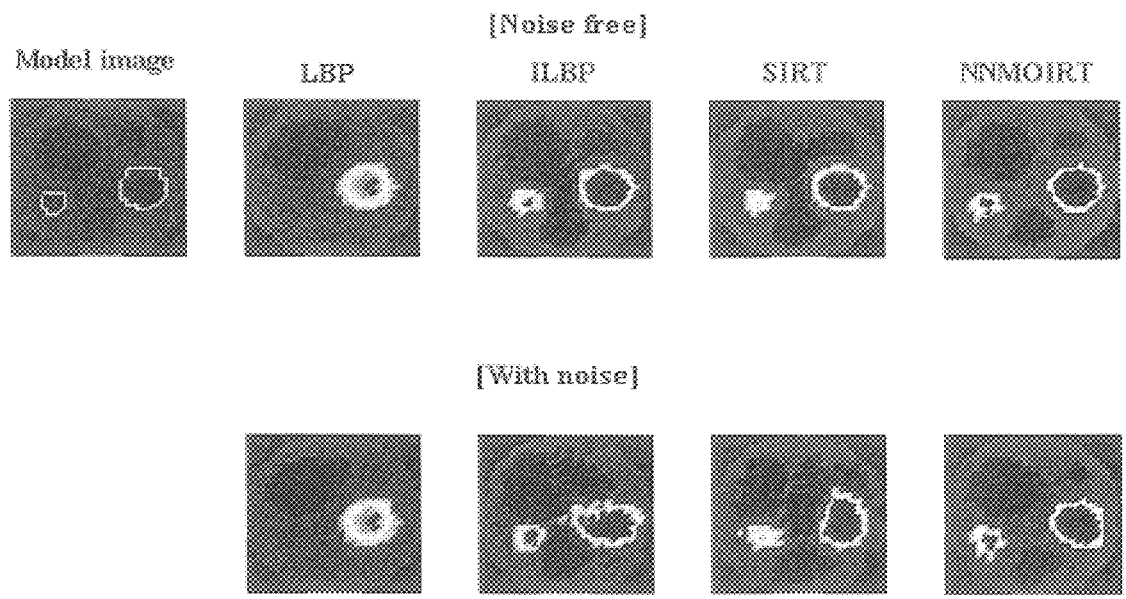
FIG. 8 compares reconstructed results for three-phase imaging using LBP, ILBP, SIRT and NN-MOIRT.

FIG. 8 shows reconstruction results for three-phase flow system model employing gas bubbles and solid particles in oil with the relative permittivities of 1, 6 and 2, respectively. The simulated capacitance data is applied to the four reconstruction techniques to compare the performance of the techniques for three-component imaging. Three thresholds to classify the reconstructed permittivity values into three regions corresponding to the three components are applied: 0~0.1 for gas, 0.2~0.5 for oil, and 0.75~1.0 for solid. For noise free capacitance data, it is seen that LBP could roughly estimate large bubble or particle in oil from the permittivity values. ILBP and SIRT could differentiate accurately large as well as small solid particles with high permittivity from gas and oil with much lower permittivities. However, they hardly differentiate the gas bubbles from oil since their permittivities are similar. Clearly, NN-MOIRT could precisely differentiate among the three components for large as well as small sizes of bubbles or particles in oil.

When noise is added, again LBP shows its robustness to the noise but only gives rough estimate of large bubbles or particles. ILBP and SIRT could only roughly differentiate the solid particles among other phases in the existence of the noise. There is not much influence of the noise to the accuracy and consistency for NN-MOIRT.

A new image reconstruction technique for imaging two- and three-phase flows using electrical capacitance tomography (ECT) developed in this work has been described. The reconstruction technique is implementing multi-criteria optimization solved by modified Hopfield neural network. The reconstruction technique is also extended to develop a reconstruction technique for three-component imaging, by replacing the single-step sigmoid function in the Hopfield networks with a double-step sigmoid function, allowing the neural computation to converge to three-distinct stable regions in the output space corresponding to the three components, enabling the differentiation among the single phases. Comparisons with other commonly used reconstruction techniques have shown its superiority in the accuracy and the consistency and its robustness to noise over other techniques. The same technique is also applicable for electrical resistance tomography (ERT).

For three-phase system applications, this technique is limited to bubbles or particles with sizes larger than the minimal spatial resolution of the capacitance tomography, which is usually between 5 to 10% of the column diameter for the best results. The other limitation of the technique is due to the large computation load involving multi-criteria objective functions. However, the technique has an advantage with respect to the computation time because the computation using a neural network is hardware realizable and inherently parallel.

While the invention has been described in connection with what is presently considered to be the most practical and preferred embodiments, it is to be understood that the invention is not to be limited to the disclosed embodiment, but on the contrary, is intended to cover various modifications and equivalent arrangements included within the spirit and scope of the appended claims, which are incorporated herein by reference.

REFERENCES

1. Beck, M. S. 1995, "Selection of sensing techniques" in *Process Tomography—Principles, Techniques and Applications*, Butterworth-Heinemann, Oxford, UK, 41–48.
2. Beck, M. S. and Williams, R. A. 1996, "Process tomography: a European innovation and its applications," *Meas. Sci. Technol.* 7, 215–224.
3. Dyakowski, T., Luke, S. P., Ostrowski, K. L. and Williams, R. A. 1999, "On-line monitoring of dense phase flow using real time dielectric imaging," *Powder Technol.* 104, 287–295.
4. Dyakowski, T., Edwards, R. B. Xie, C. G., and Williams, R. A. 1997, "Application of capacitance tomography to gas-solid flows," *Chem. Eng. Sci.* 52, 2099–2110.
5. Fan, L.-S. 1989, *Gas-liquid-solid fluidization engineering*, Butterworth, Stoneham, Me.
6. Fan, L.-S., Yang, G. Q, Lee, D. J. Tsuchiya, K. and Luo, X. 1999, "Some aspects of high-pressure phenomena of bubbles in liquids and liquid-solid suspensions," *Chem. Eng. Sci.* 54, 4681–4709.
7. George, D. L., Torczynski, J. R., Shollenberger, K. A., O'hem, T. J. and Ceccio, S. L. 2000, *Quantitative tomographic measurements of opaque multiphase flows Sandia, Report SAND*2000-0441, Sandia Nat'l Laboratories.
8. Gordon, R., Bender, R. and Herman, G. T. 1970, "Algebraic reconstruction techniques (ART) for three-dimensional electron microscopy and X-ray photography," *J. Theor. Biol.* 29, 471–481.
9. Haow, J. S. and Nicoletti, P. 1992, "Observations of fluidized-bed coalescence using capacitance imaging," *Powder Technol.* 69, 255–277.
10. Herman, G. T. 1980, *Image reconstruction from projections*, Academic Press, NY, USA.
11. Hopfield, J. 1984, "Neurons with graded response have collective computation properties like those of two-state neurons," *Proc. Nat'l Academy of Sci.* 81, May, 3088–3092.
12. Hopfield, J. and Tank. D. 1985, ""Neural" computation of decisions in optimization problems," *Biological Cybernetics* 52, 141–152.
13. Huang, S. M., Plaskowski, A., Xie, C. G. and Beck, M. S. 1989, "Tomographic imaging of two-component flow using capacitance sensors," *J. Phs. E: Sci. Instrum.* 22, 173–177.
14. Isaksen, Ø. 1996, "A review of reconstruction techniques for capacitance tomography," *Meas. Sci. Technol.* 7, 325–337.

15. Johansen, G. A., Froystein, T., Hjertaker, B. T. and Olsen, Ø. 1996, "A dual sensor flow imaging tomographic system," *Meas. Sci. Technol.* 7, 297–307.
16. Liang, Y. 1996, "Combinatorial optimization by Hopfield networks using adjusting neurons," *Information Sci.* 94, 261–276.
17. Liu, S., Fu, L. and Yang, W.Q. 1999, "Optimization of an iterative image reconstruction algorithm for electrical capacitance tomography," *Meas. Sci. Technol.* 10, L37-L39.
18. Mwambela, A. J., Isaksen, Ø. And Johansen, G. A. 1997, "The use of entropic thresholding methods in reconstruction of capacitance tomography data," *Chem. Eng. Sci.* 52, 2149–2159.
19. Nooralahiyan, A. Y. and Hoyle, B. S. 1997, "Three-compoent tomographic flow imaging using artificial neural network reconstruction," *Chem. Eng. Sci.* 52, 2139–2148.
20. Ostrowski, K. L., Luke, S. P. and Williams, R. A. 1997, "Simulation of the performance of electrical capacitance tomography for measurement of dense pneumatic conveying," *Chem. Eng. J.* 68, 197–205.
21. Paik, J. K and Katsagelos, A. K. 1992, "Image reconstruction using a modified Hopfield networks," *IEEE Trans. Image Process.* 1, 49–63.
22. Process Tomography Ltd. 1999, *Application Note AN4—An iterative method for improving ECT images*, PTL, Cheshire, UK.
23. Reinecke, N. and Mewes, D. 1996, "Recent development and industrial/research applications of capacitance tomography", *Meas. Sci. Technol.* 7, 233–246.
24. Reinecke, N. and Mewes, D. 1996, "Recent development and industrial/research applications of capacitance tomography," *Meas. Sci. Technol.* 7, 1996, 233–246.
25. Smith, K., Krishnamoorthy, M. and Palaniswami, M. 1996, "Neural versus traditional approaches to the location of interacting hub facility," *Location Sci.* 4, 155–171.
26. Su, B., Zhang, Y., Peng. L., yao, D. and Zhang, B. 2000, "The use of simultaneous iterative reconstruction technique fr electrical capacitance tomography," *Chem. Eng. J.* 77, 37–41.
27. Sun, Y., Li. J.-G. and yu, S.-Y. 1995, "Improvement on performance of modified Hopfield neural network for image restoration," *IEEE Trans. Image Process.* 4, 688–692.
28. Wang, S. J., Dyakowski, T., Xie, C. G., Williams, R. A. and Beck, M.S. 1995, "Real time capacitance imaging of bubble formation at the distributor of fluidized bed," *Chem. Eng. J.* 56, 95–100.
29. Wang, Y. 1997, "Multicriteria neural network approach to turbulent image reconstruction," *Optics Commun.* 143, 279–286.
30. Wang, Y. 1998, "Neural network approach to image reconstruction from projections," *Int. J. Imaging system and Technol.* 9, 381–387.
31. Warsito, Maezawa, A., Uchida, S. and Okamura, S. 1995, "A model of simultaneous measurement of gas and solid holdups in a bubble column using ultrasonic technique," *Can. J. Chem. Eng.* 73, 734–743.
32. Warsito, Ohkawa, M., Kawata, N. and Uchida, S.: "Cross-sectional distributions of gas and solid holdups in slurry bubble column investigated by ultrasonic computed tomography", *Chem. Eng. Sci.*, Vol.54, 4711–4728 (1999).
33. Williams, R. A. and Beck, M. S. 1995, *Process Tomography—Principles, Techniques and Applications*, Butterworth-Heinemann, Oxford, UK.
34. Xie, C. G. 1995, "Image reconstruction," in *Process Tomography—Principles, Techniques and Applications*, Williams, R. A. and Beck, M. S., Butterworth-Heinemann, Oxford, UK, 281–323.
35. Xie, C. G., Huang, S. M., Hoyle, B. S., Thorn, R., Lean, C., Snowden, D. and Beck, M. S. 1992, "Electrical capacitance tomography for floe imaging system model for development of image reconstruction algorithms and design of primary sensor," *IEE Proc. G* 139, 89–98.
36. Xie, C. G., Reinecke, N., Beck, M. S. Mewes, D. and Williams, R. A. 1995, "Electrical tomography techniques for process engineering applications," *Chem. Eng. J.* 56, 127–133.
37. Yang, W. Q., Spink, D. M., York, T. A. and McCann, H. 1999, "An image reconstruction algorithm based on Landweber's iteration method for electrical-capacitance tomography," *Meas. Sci. Technol.* 10, 1065–1069.
38. Yang, W. Q., Stott, A. L., Beck, M. S. and Xie, C. G. 1996, "Development of capacitance tomography imaging systems for oil pipeline measurements", *Int. J. Multiphase Flow* 2, Supplem. 1, 144–145.
39. Zhou, Y.-T, Chellapa, R., Vaid. and Jenkins, B. K. 1998, "Image restoration using a neural network," *IEEE Trans. Acoust. Speech Signal Process.* 36, 1141–1151.

The foregoing references are hereby incorporated herein by reference.

What is claimed is:

1. A method for image reconstruction comprising:
   (a) obtaining image measurement data;
   (b) processing said image measurement data by application of a linear back projection algorithm with a Hopfield model neural network; and
   (c) displaying said processed image data on a display device.

2. A method according to claim 1, wherein said image measurement data is selected from the group consisting of: capacitance data, conductance data, x-ray data, gamma-ray data, ultrasonic data and optical data.

3. A method according to claim 1, wherein said linear back projection algorithm is a back projection algorithm in which a sensitivity matrix is used.

4. A method according to claim 1, wherein said Hopfield model neural network comprises selecting at least one function to minimize.

5. A method according to claim 4, wherein said at least one function comprises a negative entropy function, a weighted square error function, and a sum of non-uniformity and peakedness function.

6. A method according to claim 1, wherein said Hopfield model neural network is modified to include a penalty function that permits a temporary increase in a descending evolution of a Hopfield network energy to allow escape from local minima.

7. A method according to claim 1, wherein said display device is selected from the group consisting of: monitors, CRTs, plotters, and printers.

8. A method for obtaining a cross-sectional image of a two-phase fluid flowing through a conduit having an interior, said method comprising:
   (a) acquiring image measurement data from at least two sensors peripherally located on said interior of said conduit, said at least two sensors defining a cross-section of said conduit;
   (b) sending said image measurement data to a processing unit;

(c) processing said image measurement data, said processing comprising a simultaneous minimization of:
  (i) a negative entropy function of an image given by $$f_1(G) = \gamma_1 \sum_{j=1}^{N} G_j \ln G_j$$

where $\gamma_1$ is a normalized constant between 0 and 1;
  (ii) a weighted square error function given by $$f_2(G) = \frac{1}{2}\gamma_2 \sum_{i=1}^{M} \left( \sum_{j=1}^{N} S_{ij} G_j - C_i \right)^2$$

where $\gamma_2$ is a normalized constant between 0 and 1;
  (iii) a sum of non-uniformity and peakedness functions given by $$f_3(G) = \frac{1}{2}\gamma_3 (G^T X G + G^T G)$$

where $\gamma_3$ is a normalized constant between 0 and 1;
  by application of a Hopfield model given by $$E(G) = \sum_{l=1}^{3} \omega_l f_l(G) + \sum_{i=1}^{M} \Psi(z_i) + \sum_{j=1}^{N} \frac{1}{R_j} \int_{0}^{G_j} f_\Sigma^{-1}(G) dG$$

wherein normalized permittivity values are mapped into output variables using a single sigmoid function given by $$f_\Sigma(u_j) = \frac{1}{1 + \exp(-\beta u_j)},$$

to force convergence to a binary output, said Hopfield model further comprising a penalty function $\Psi(z_i)$ defined as $$\Psi(z_i) = \begin{cases} 0 & \text{if } z_i \leq 0 \\ \alpha z_i & \text{if } z_i > 0 \end{cases}$$

where $$z_i = \sum_{j=1}^{N} S_{ij} G_j - C_i$$

with $\alpha(t) = \alpha_0 + \xi \exp(-\eta t)$ where $\alpha_0$, $\xi$, and $\eta$ are positive constants, said penalty function preventing convergence at local minima; and
(d) outputting said output variables to a display device to form a cross-sectional image of said two-phase fluid flowing through said conduit.

9. The method according to claim 8 wherein said image measurement data is selected from the group consisting of: capacitance data, conductance data, x-ray data, gamma-ray data, ultrasonic data and optical data.

10. The method according to claim 8 wherein said two-phase fluid comprises a solid phase and a liquid phase.

11. The method according to claim 8 wherein said two-phase fluid comprises a liquid phase and a gaseous phase.

12. The method according to claim 8 wherein said two-phase fluid comprises a solid phase and a gaseous phase.

13. The method according to claim 8 wherein said two-phase fluid comprises a first solid phase and a second solid phase.

14. The method according to claim 8 wherein said two-phase fluid comprises a first liquid phase and a second liquid phase.

15. The method according to claim 8 wherein said two-phase fluid comprises a first gaseous phase and a second gaseous phase.

16. The method according to claim 8 wherein said display device is selected from the group consisting of: monitors, projectors, printers and plotters.

17. A method for obtaining a cross-sectional image of a three-phase fluid flowing through a conduit having an interior, said method comprising:
  (a) acquiring image measurement data from at least two sensors peripherally located on said interior of said conduit, said at least two sensors defining a cross-section of said conduit;
  (b) sending said image measurement data to a processing unit;
  (c) processing said image measurement data, said processing comprising a simultaneous minimization of:
    (1) a negative entropy function of an image given by $$f_1(G) = \gamma_1 \sum_{j=1}^{N} G_j \ln G_j$$

where $\gamma_1$ is a normalized constant between 0 and 1;
    (2) a weighted square error function given by $$f_2(G) = \frac{1}{2}\gamma_2 \sum_{i=1}^{M} \left( \sum_{j=1}^{N} S_{ij} G_j - C_i \right)^2$$

where $\gamma_2$ is a normalized constant between 0 and 1;
    (3) a sum of non-uniformity and peakedness functions given by $$f_3(G) = \frac{1}{2}\gamma_3 (G^T X G + G^T G)$$

where $\gamma_3$ is a normalized constant between 0 and 1;
  by application of a Hopfield model given by $$E(G) = \sum_{l=1}^{3} \omega_l f_l(G) + \sum_{i=1}^{M} \Psi(z_i) + \sum_{j=1}^{N} \frac{1}{R_j} \int_{0}^{G_j} f_\Sigma^{-1}(G) dG$$

wherein normalized permittivity values are mapped into output variables using a double sigmoid function given by $f_\Sigma(u_j) = f_{\Sigma 1}(u_j) + f_{\Sigma 2}(u_j)$, where $$f_{\Sigma 1}(u_j) = \frac{\rho_1}{1 + \exp(-\beta_1(u_j + \xi_1))},$$

$$f_{\Sigma 2}(u_j) = \frac{\rho_2}{1 + \exp(-\beta_2(u_j + \xi_2))},$$

$\rho_1$ and $\rho_2$ are positive constants, $\beta_1$ and $\beta_2$ are steepness gains of sigmoid functions $f_{\Sigma 1}$ and $f_{\Sigma 2}$, and $\xi_1$ and $\xi_2$ are parameters, where said double sigmoid function purpose is to force convergence to a tertiary output, said Hopfield model further comprising a penalty function $\Psi(z_i)$ defined as $$\Psi(z_i) = \begin{cases} 0 & \text{if } z_i \leq 0 \\ \alpha z_i & \text{if } z_i > 0 \end{cases}$$

where $$z_i = \sum_{j=1}^{N} S_{ij} G_j - C_i$$

with $\alpha(t)=\alpha_0+\xi\,\exp(-\eta t)$ where $\alpha_0$, $\xi$, and $\eta$ are positive constants, said penalty function preventing convergence at local minima; and (d) outputting said output variables to a display device to form a cross-sectional image of said three-phase fluid flowing through said conduit.

18. The method according to claim 17, wherein said image measurement data is selected form the group consisting of: capacitance data, conductance data, x-ray data, gamma-ray data, ultrasonic data and optical data.

19. The method according to claim 17 wherein said display device is selected from the group consisting of: monitors, projectors, printers and plotters.

20. The method according to claim 17 wherein said three-phase flow comprises a solid phase, a liquid phase, and a gaseous phase.

21. The method according to claim 17 wherein said three-phase flow comprises a first solid phase, a second solid phase and a third solid phase.

22. The method according to claim 17 wherein said three-phase flow comprises a first solid phase, a second solid phase and a first liquid phase.

23. The method according to claim 17 wherein said three-phase flow comprises a first solid phase, a first liquid phase and a second liquid phase.

24. The method according to claim 17 wherein said three-phase flow comprises a first solid phase, a second solid phase and a first gaseous phase.

25. The method according to claim 17 wherein said three-phase flow comprises a first solid phase, a first gaseous phase and a second gaseous phase.

26. The method according to claim 17 wherein said three-phase flow comprises a first liquid phase, a second liquid phase and a first gaseous phase.

27. The method according to claim 17 wherein said three-phase flow comprises a first liquid phase, a first gaseous phase and a second gaseous phase.

28. The method according to claim 17 wherein said three-phase flow comprises a first liquid phase, a second liquid phase and a third liquid phase.

29. The method according to claim 17 wherein said three-phase flow comprises a first gaseous phase, a second gaseous phase and a third gaseous phase.

30. A method for obtaining a cross-sectional image of a multiphase fluid flowing through a conduit having an interior using a Hopfield model neural network, said method comprising:

(a) acquiring image measurement data for fluid flowing through a conduit, said image measurement data acquired by at least two sensors peripherally located on said interior of said conduit, said at least two sensors defining a cross-section of said conduit;

(b) initializing a neural network by:
(1) choosing an initial state of neurons;
(2) setting at least one steepness gain factor;
(3) initializing a penalty parameter;
(4) initializing an initial gain factor;

(c) updating an image vector; and (d) stopping when $|G_j(t+\Delta t)-G_j(t)|^2 \leq e$ for all neurons, where $|G_j(t+\Delta t)-G_j(t)|^2$ is error and e is a termination scalar set by an operator; and (e) displaying said image vector.

31. The method according to claim 30, wherein said image measurement data is selected from the group consisting of: capacitance data, conductance data, x-ray data, gamma-ray data, ultrasonic data and optical data.

32. The method according to claim 30 wherein said initial state of neurons is determined experimentally.

33. The method according to claim 30 wherein said steepness gain factor 6 is determined experimentally.

34. The method according to claim 30 wherein said initial state of said penalty parameter is determined experimentally.

35. The method according to claim 30 wherein said initial state of said gain factor is determined experimentally.

36. The method according to claim 30 wherein said multiphase fluid consists of solids and liquids.

37. The method according to claim 30 wherein said multiphase fluid consists of solids and gases.

38. The method according to claim 30 wherein said multiphase fluid consists of liquids and gases.

39. The method according to claim 30 wherein said multiphase fluid consists of solids.

40. The method according to claim 30 wherein said multiphase fluid consists of liquids.

41. The method according to claim 30 wherein said multiphase fluid consists of gases.

42. The method according to claim 30 wherein said multiphase fluid consists of solids, liquids and gases.

43. The method according to claim 30 wherein said updating of said imaging vector comprises:

(a) calculating coefficients of objective functions:

$$\gamma_1^{(t+\Delta t)} = \left[\sum_{j=1}^{N} G_j(t)\ln G_j(t)\right]^{-1}, \quad \gamma_2^{(t+\Delta t)} = \left[\frac{1}{2}\|SG(t)-C\|^2\right]^{-1},$$

$$\gamma_3^{(t+\Delta t)} = \left[\frac{1}{2}G^T(t)sG(t) + \frac{1}{2}G^T(t)G(t)\right]^{-1};$$

(b) updating weights $\omega_1,\omega_2,\omega_3$ for every iteration as follows:

$$\omega_i^{(t+\Delta t)} = \frac{\Delta\omega_1^{(t)}/\Delta\omega_i^{(t)}}{\sum_{i=1}^{3}\Delta\omega_1^{(t)}/\Delta\omega_i^{(t)}},$$

$\Delta\omega_i^{(t)}={}^{-f}{}_i(G)(t-\Delta t))$, (i=1,2,3) where $f_1$ is a negative entropy function, $f_2$ is a weighted square error function and $f_3$ is a sum of non-uniformity and peakedness functions of an image; and (c) calculating an image vector $G_j(t+\Delta t)$, where $G_j(t+\Delta t)=G_j(t)+f'_\Sigma(u)u'_j(t)\Delta t$, $f'_\Sigma(u)=df_\Sigma(u_j)/du_j$ and $u'_j(t)=du_j(t)/dt$.

44. The method according to claim 30 wherein said steepness gain factors $\beta_1$ and $\beta_2$ are determined experimentally.

45. The method according to claim 30 wherein said multiphase fluid consists of solids, liquids and gases or combinations thereof.

46. The method according to claim 30 wherein said updating of said imaging vector comprises:

(a) calculating coefficients of objective functions:

$$\gamma_1^{(t+\Delta t)} = \left[\sum_{j=1}^{N} G_j(t)\ln G_j(t)\right]^{-1}, \quad \gamma_2^{(t+\Delta t)} = \left[\frac{1}{2}\|SG(t)-C\|^2\right]^{-1},$$

$$\gamma_3^{(t+\Delta t)} = \left[\frac{1}{2}G^T(t)sG(t) + \frac{1}{2}G^T(t)G(t)\right]^{-1};$$

(b) updating weights $\omega_1, \omega_2, \omega_3$ for every iteration as follows:

$$\omega_i^{(t+\Delta t)} = \frac{\Delta\omega_1^{(t)}/\Delta\omega_i^{(t)}}{\sum_{i=1}^{3}\Delta\omega_1^{(t)}/\Delta\omega_i^{(t)}},$$

$\Delta\omega_i^{(t)} = f_i(G)(t-\Delta t)) - f_i(G)(t))$, (i=1,2,3) where $f_1$ is a negative entropy function, $f_2$ is a weighted square error function and $f_3$ is a sum of non-uniformity and peakedness functions of an image; and (c) calculating an image vector $G_j(t+\Delta t)$, where $$G_j(t+\Delta t) = f_\Sigma(u_j(t+\Delta t)) = G_j(t) +$$
$$[f_{\Sigma 1}(u_j)(1-f_{\Sigma 1}(u_j)) + f_{\Sigma 2}(u_j)(1-f_{\Sigma 2}(u_j))]u_j(t)\Delta t,$$

$$f_{\Sigma 1}(u_j) = \frac{\rho_1}{1+\exp(-\beta_1(u_j+\xi_1))},$$

$$f_{\Sigma 2}(u_j) = \frac{\rho_2}{1+\exp(-\beta_2(u_j+\xi_2))},$$

$\rho_1 = \widetilde{\epsilon}_{0M}$, and $\rho_2 = 1 - \widetilde{\epsilon}_{0M}$.

\* \* \* \* \*